United States Patent [19]

Cron et al.

[11] 4,424,343
[45] * Jan. 3, 1984

[54] PREPARATION OF 1-N-[ω-AMINO-α-HYDROXYALKANOYL]-KANAMYCIN POLYSILYLATES AND PRODUCTS

[75] Inventors: Martin J. Cron, Fayetteville; John G. Keil, Manlius; Jeng S. Lin, Clay; Mariano V. Ruggeri, Liverpool; Derek Walker, Jamesville, all of N.Y.

[73] Assignee: Bristol Myers Company, New York, N.Y.

[ * ] Notice: The portion of the term of this patent subsequent to Aug. 31, 1999, has been disclaimed.

[21] Appl. No.: 203,098

[22] Filed: Nov. 3, 1980

Related U.S. Application Data

[63] Continuation of Ser. No. 8,730, Feb. 2, 1979, abandoned, which is a continuation-in-part of Ser. No. 888,585, Mar. 20, 1978, abandoned, and Ser. No. 896,430, Apr. 14, 1978, abandoned, each is a continuation-in-part of Ser. No. 791,806, Apr. 28, 1977, abandoned.

[51] Int. Cl.$^3$ ............................................ C07H 15/22
[52] U.S. Cl. .................................. 536/13.8; 424/180; 536/13.7
[58] Field of Search ...................... 536/10, 17 R, 13.7, 536/13.8

[56] References Cited

U.S. PATENT DOCUMENTS

| | | | |
|---|---|---|---|
| 4,029,882 | 6/1977 | Wright ................................. | 536/17 |
| 4,029,883 | 6/1977 | Hiraga et al. ......................... | 536/17 |
| 4,055,715 | 10/1977 | Tomioka et al. ..................... | 536/17 |
| 4,347,354 | 8/1982 | Cron et al. ............................ | 536/10 |

OTHER PUBLICATIONS

Murata et al., "Chem. Abst.", vol. 79, 1973, p. 83498(y).

*Primary Examiner*—Johnnie R. Brown
*Attorney, Agent, or Firm*—Richard R. Lloyd

[57] ABSTRACT

An improved process for the preparation of 1-N-[ω-amino-α-hydroxyalkanoyl]kanamycins comprises acylating a polysilylated kanamycin in a substantially anhydrous organic solvent with an acylating derivative of an ω-amino-α-hydroxyalkanoic acid.

21 Claims, No Drawings

PREPARATION OF 1-N-[ω-AMINO-α-HYDROXYALKANOYL]KANAMYCIN POLYSILYLATES AND PRODUCTS

CROSS-REFERENCE TO RELATED APPLICATION

This application is a continuation of our prior copending application Ser. No. 8,730, filed Feb. 2, 1979, which is a continuation-in-part of our prior, co-pending applications Ser. No. 888,585, filed Mar. 20, 1978, and Ser. No. 896,430, filed Apr. 14, 1978, each of which is a continuation-in-part of our prior, co-pending application Ser. No. 791,806, filed Apr. 28, 1977, and all now abandoned.

SUMMARY OF THE INVENTION

This invention relates to an improved process for the preparation of compounds of the formula

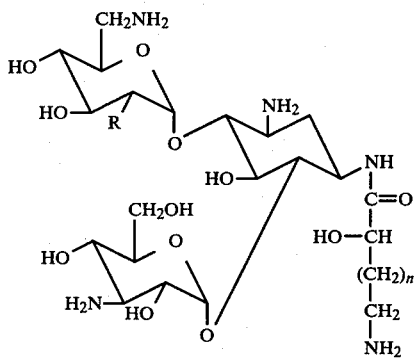

in which R is OH or $NH_2$ and n is an integer of from 0 to 2, or a nontoxic pharmaceutically acceptable acid addition salt thereof, which comprises acylating polysilylated kanamycin A or B, or polysilylated kanamycin A or B containing a conventional non-silyl blocking group on the 3-amino group, the 6'-amino group or the 3-amino and 6'-amino groups, in a substantially anhydrous organic solvent, with an acylating derivative of an acid of the formula

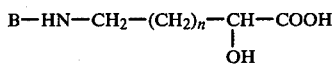

in which n is an integer of from 0 to 2 and B is a conventional amino-blocking group, and subsequently removing all blocking groups by conventional means.

DESCRIPTION OF THE PRIOR ART

The kanamycins are well-known antibiotics, having been described, for example in the Merck Index, 8th edition, pp. 597–8. Numerous derivatives of the kanamycins also are known. The structural formulae of kanamycins A and B are given below, along with the standard numbering system used in the art. Hereinafter, where readily understandable, the various kanamycin derivatives will be referred to as derivatives of kanamycin A or B rather than by structural formula, so as to avoid the necessity of comparing complex structures to determine differences.

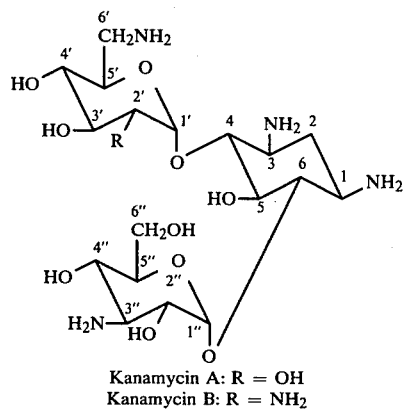

Kanamycin A: R = OH
Kanamycin B: R = $NH_2$

U.S. Pat. No. 3,781,268 discloses and claims 1-[L-(−)-γ-amino-α-hydroxybutyryl]kanamycin A (amikacin) and B, as well as their mono- and di-carbobenzyloxy protected derivatives. For lower and higher homologs see U.S. Pat. Nos. 3,886,139 and 3,904,597. The compounds are prepared by acylating a 6'-N-protected kanamycin A or B with an acylating derivative of an N-protected L-(−)-γ-amino-α-hydroxybutyric acid, in an aqueous medium, followed by removal of one or both N-protecting groups.

U.S. Pat. No. 3,974,137 discloses and claims a process for preparing 1-[L-(−)-γ-amino-α-hydroxybutyryl]-kanamycin A which comprises reacting 6'-carbobenzyloxykanamycin A with at least three moles of benzaldehyde, a substituted benzaldehyde or pivaldehyde, to produce 6'-N-carbobenzyloxykanamycin A containing Schiff base moieties on the 1,3 and 3"-positions, acylating this tetra-protected kanamycin A derivative with the N-hydroxysuccinimide ester of L-(−)-γ-benzyloxycarbonylamino-α-hydroxybutyric acid, and subsequently removing the protecting groups.

Belgian Patent 828192 discloses and claims a process for preparing 1-[L-(−)-γ-amino-α-hydroxybutyryl[-kanamycin A by preparation of the same tetra-protected kanamycin A derivative as in U.S. Pat. No. 3,974,137, acylating with the N-hydroxy-5-norbornene-2,3-dicarboximide ester of L-(−)-γ-benzyloxycarbonylamino-α-hydroxybutyric acid, and subsequently removing the protecting groups.

U.S. Pat. No. 3,939,143 discloses and claims 1-N-isoseryl (1-N-β-amino-α-hydroxypropionyl) derivatives of kanamycin A, kanamycin B and 3',4'-dideoxykanamycin B, and their preparation by acylating the appropriate 6'-N-blocked or 2',6'-di-N-blocked kanamycin with an acylating derivative of an N-protected isoserine, in an aqueous medium, and subsequently removing the N-protecting groups.

Trimethylsilyl derivatives of various aminoglycoside antibiotics, including the kanamycins, are known. They have been prepared to impart volatility to these relatively non-volatile compounds, for purposes of gas chromatography and mass spectroscopy analyses.

Bunseki Kagaku, 22, 405–410 (1973), [Chemical Abstracts, 79, 83498y (1973)] reports gas chromatography and mass spectroscopy analyses of trimethylsilyl derivatives of kanamycin A, kanamycin B and neomycin B. These were persilylated compounds in which all hydroxy and amino groups were silylated.

In J. Am. Chem. Soc., 89, 3364–5 (1967), D. C. DeJongh et al. report on mass spectrometric structural analysis studies conducted on the per(N-acetyl)-per(O-trimethylsilyl) derivatives of paromomycin and paromomycin II.

In Tetrahedron Letters, No. 46, pp 4009-12 (1974), T. Takamoto and S. Hanessian, report the conversion of paromomycin into a pseudotrisaccharide by elimination of the diaminohexose unit, and the confirmation of its structure by high resolution mass spectroscopic analysis of its per(N-acetyl)-per(O-trimethylsilyl) derivative. On pages 4013-6 of the same volume, T. Ogawa et al. report the preparation of a positional isomer of the above pseudotrisaccharide and confirmation of its structure by high resolution mass spectroscopy of its per(N-acetyl)-per(O-trimethylsilyl) derivative.

In The Journal of Antibiotics, 28, 522-9 (1975) P. W. K. Woo describes the synthesis of 5″-amino-3′,4′,5″-trideoxybutirosin and report that its structure is consistent with the mass spectrum of its penta-N-acetyl-tetrakis-O-trimethylsilyl derivative.

In The Journal of Antibiotics, 26, 374-385 (1973), S. Inouye et al. report the isolation of a new member of the destomycin group of aminoglycosides from a culture broth of Streptomyces eurocidicus SS-56. Its structure was elucidated by means of gas chromatography of its per(trimethylsilyl) derivative and mass spectroscopy of the per(O-trimethylsilyl)-N-salicylidene Schiff base derivative.

In The Journal of Antibiotics, 26, 784-6 (1973), M. Kojima and A. Satoh report the semi-synthesis of several aminoglycoside antibiotics (e.g. 6′-deamino-6′-hydroxy-1-N-methylkanamycin) by the addition of deoxystreptamine or neamine analogs to fermentation broths of deoxystreptamine-negative mutants of Streptomyces ribosidifucus and Streptomyces kanamyceticus. Their structures were elucidated by mass spectroscopy of their N-acetyl-O-trimethylsilyl derivatives.

In Analytical Chemistry, 42, 1661-3 (1970), K. Tsuji and J. H. Robertson describe a method for the separation and determination of the kanamycins and paromomycins by silylation and gas chromatography of the per(trimethylsilyl) derivatives.

In Proc. Nat. Acad. Sci., 63, 198-204 (1969), W. T. Shier et al. report the preparation of hybrimycins A1, A2, B1 and B2 by fermentation of a mutant of Streptomyces fradiae, and mass spectroscopic analysis of their N-acetyl-per(O-trimethylsilyl) derivatives.

In The Journal of Antibiotics, 26, 790-3 (1973), T. P. Culbertson et al. report the preparation of 5″-amino-5″-deoxybutirosins A and B from butirosins A and B. The first steps in the synthesis involved:

(1) partially N-trifluoroacetylating butirosin base by refluxing in a mixture of methanol and ethyl trifluoroacetate, (2) evaporating to dryness, dissolving the residue in pyridine, treating it with hexamethyldisilizane and trimethylchlorosilane, then cooling to <10° C. and treating it with trifluoroacetic anhydride, (3) evaporating to dryness and hydrolyzing the residue in a 2:1 mixture of ethanol and 2 N acetic acid at reflux, to give tetra[N-(trifluoroacetyl)]butirosin.

The final products of the synthetic scheme, 5″-amino-5″-deoxybutirosins A and B, also were reacted according to the above three steps to give penta[N-(trifluoroacetyl)]-5″-amino-5″-deoxybutirosins A and B. Although this publication discloses the acylation of a trimethylsilylated (and partially acylated) aminoglycoside antibiotic, the result in each instance is complete acylation of all primary amino groups in the molecule (four in the starting butirosin and five in the product). The process of the present invention substantially eliminates polyacylation and provides a high degree of selectivity of acylation in the desired 1-N-position.

J. J. Wright et al., in The Journal of Antibiotics, 29, 714-719 (1976), describe a general procedure for the selective 1-N-acylation of the gentamicin-sisomicin class of aminoglycosides. They report that selectivity in the site of acylation is pH dependent and that the C-1 amino group is the most reactive toward acylation when the amino groups of the molecule are almost completely protonated. These conditions are achieved by the addition of one equivalent of a tertiary amine base to a solution of the fully neutralized acid addition salt. Although these workers obtained 1-N-selectivity in the acylation of gentamicin $C_{1a}$, sisomicin and verdamicin, they reported that little selectivity was observed in the acylation of highly hydroxylated aminoglycosides such as gentamicin B and kanamycin A.

U. K. Pat. No. 1,460,039 discloses a process for the preparation of deoxyaminoglycosides, including the kanamycins, by halogenating a phosphorylated aminoglycoside (one in which the hydroxy group to be removed has been converted to a phosphonoxy group), to produce the corresponding aminoglycoside in which the hydroxy group has been converted to halogen, and reducing the halogen compound to produce the corresponding deoxyaminoglycoside. Before halogenating the phosphorylated aminoglycoside, all of its functional groups are preferably protected by means of silyl or acyl groups.

DETAILED DESCRIPTION

The present invention provides an improved and commercially attractive process for the preparation of compounds of formula I. The use of a polysilylated kanamycin A or B as a starting material gives high solubility in the organic solvent system, thus permitting reaction at high concentrations. Although the reaction is usually conducted in solutions containing about 10-20% polysilylated kanamycin starting material, excellent results have been obtained at concentrations of about 50% W/V (e.g. 50 gms./100 ml. of solvent).

As with prior art processes, the present process gives a mixture of acylated products. The desired 1-N-acylated product is separated from the other products by chromatography and, if desired, the by-products may be hydrolyzed to the starting kanamycin for recycling. In prior art processes it was found that any 3″-N-acylated material which was produced caused a loss of about an equal amount of the desired 1-N-acylated product, due to the great difficulty of separating the latter from the former. Thus, in preparing 1-[L-(−)-γ-amino-α-hydroxybutyryl]kanamycin A (BB-K8) by various prior art procedures, there is typically also produced the 3″-N-acylated product (BB-K11), the 3-N-acylated product (BB-K29), the 6′-N-acylated product (BB-K6) and polyacylated material, as well as unreacted kanamycin A. Thus, in commercial production of BB-K8 by acylation of 6′-N-carbobenzyloxy kanamycin A in an aqueous medium, followed by removal of the protecting group, we found that about 10% of the desired BB-K8 (2.5 kg. in a 25 kg. batch) usually was lost because of the presence of BB-K11 as a co-product. A particularly desirable feature of the present process is the extremely low amount of undesirable 3″-N-acylated product which is produced (typically, none is detected).

When preparing BB-K8 by the present process, BB-K11 (typically is not detected in the reaction mixture.

The present invention provides the process for the preparation of a 1-N-[ω-amino-α-hydroxyalkanoyl]-kanamycin A or B having the formula

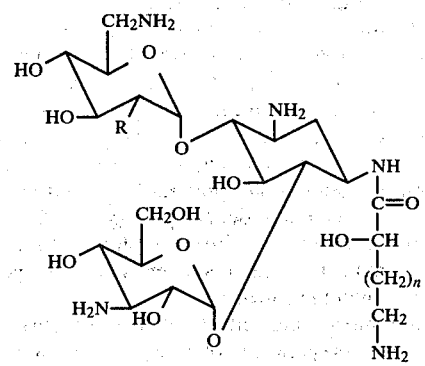

in which R is OH or NH₂ and n is an integer of from 0 to 2, or a nontoxic pharmaceutically acceptable acid addition salt thereof, which comprises acylating polysilylated kanamycin A or B or polysilylated kanamycin A or B containing a conventional non-silyl blocking group on the 3-amino group, the 6′-amino group or the 3-amino and 6′-amino groups, with an acylating derivative of the acid of the formula

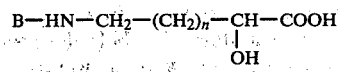

in which n is an integer of from 0 to 2 and B is a conventional amino-blocking group, in a substantially anhydrous organic solvent, and subsequently removing all blocking groups by conventional means.

The blocking groups which may be used to protect the 3- and/or 6′-amino groups of the kanamycin and the amino group of the acylating acid (group B in Formula II) are conventional blocking groups for the protection of primary amine groups and are well known to those skilled in the art. Suitable blocking groups include alkoxycarbonyl groups such as t-butoxycarbonyl and t-amyloxycarbonyl; aralkoxycarbonyl groups such as benzyloxycarbonyl; cycloalkyloxycarbonyl groups such as cyclohexyloxycarbonyl; haloalkoxycarbonyl groups such as trichloroethoxycarbonyl; acyl groups such as phthaloyl and o-nitrophenoxyacetyl; haloacetyl groups such as trifluoroacetyl; and other well-known blocking groups such as 2,4-dinitrophenyl, trityl, benzyl, alkylbenzyl, etc.. Another particularly useful class of blocking groups are those of the formula RCH= in which R is aryl or (lower)alkyl, each of which may be substituted by chloro, bromo, fluoro, nitro, (lower)alkoxy, or the like. These blocking groups, which form a Schiff base with the amino group, are introduced by reaction with the desired aldehyde, e.g. benzaldehyde or pivaldehyde.

The acylating acid of formula II may be in its (+) or (−) isomeric form or a mixture of the two isomers (the d,l form), thus producing the corresponding compound of formula I in which the 1-N-[ω-amino-α-hydroxyalkanoyl] group is in its (+) [or (R)] form or its (−) [or (S)] form, or a mixture thereof. Each such isomeric form, and the mixture thereof, is included within the scope of this invention. In one preferred embodiment, the acylating acid of formula II is in its (−) form. In another preferred embodiment the acylating acid of Formula II is in its (+) form.

In one embodiment of the invention the starting material is polysilylated kanamycin A or B (and preferably polysilylated kanamycin A). In other embodiments the starting material is polysilylated kanamycin A or B (and preferably polysilylated kanamycin A) containing a conventional non-silyl blocking group on the 3-amino group, the 6′-amino group or the 3-amino and 6′-amino groups, said blocking group preferably being selected from those of the formulae

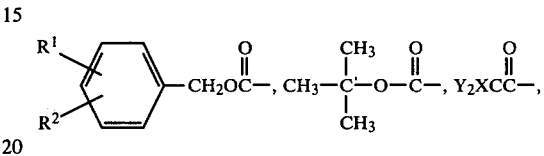

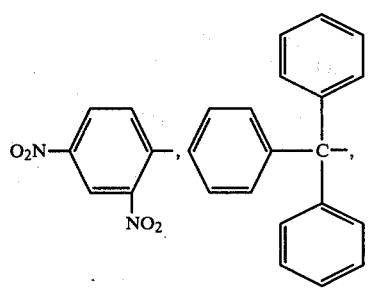

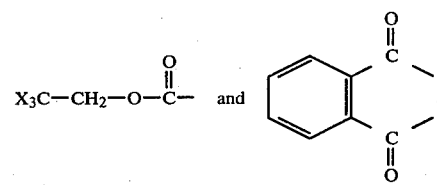

wherein R¹ and R² are alike or different and each is H, F, Cl, Br, NO₂, OH, (lower)alkyl or (lower)alkoxy, and X is Cl, Br, F or I, and Y is H, Cl, Br, F or I. The most preferred blocking group is the carbobenzyloxy group.

In a preferred embodiment of the invention the acylating derivative of the acid of Formula II is an active ester, and preferably its active ester with N-hydroxysuccinimide, N-hydroxy-5-norbornene-2,3-dicarboximide or N-hydroxyphthalimide. In another preferred embodiment the acylating derivative of the acid of Formula II is a mixed acid anhydride, and preferably its mixed acid anhydride with pivalic acid, benzoic acid, isobutylcarbonic acid or benzylcarbonic acid.

In another preferred embodiment, amino-blocking group B of the acylating derivative of the acid of Formula II is selected from blocking groups of the formulae

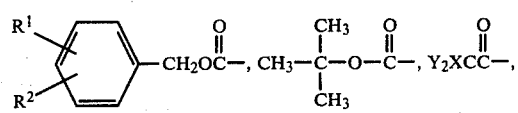

-continued

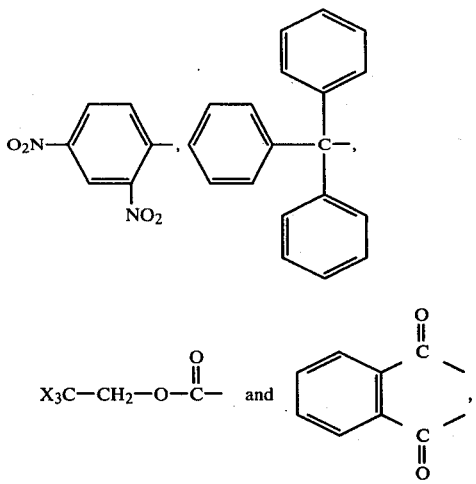

wherein $R^1$ and $R^2$ are alike or different and each is H, F, Cl, Br, $NO_2$, OH, (lower)alkyl or (lower)alkoxy, X is Cl, Br, F or I, and Y is H, Cl, Br, F or I. The most preferred blocking group is the carbobenzyloxy group.

In another preferred embodiment the acylating derivative of the acid of Formula II is an acylating derivative of N-blocked γ-amino-α-hydroxybutyric acid. In a more preferred embodiment the acylating derivative of the acid of Formula II is a mixed acid anhydride of γ-benzyloxycarbonylamino-α-hydroxybutyric acid, and most preferably its mixed acid anhydride with pivalic acid, benzoic acid, isobutylcarbonic acid or benzylcarbonic acid. In another more preferred embodiment, the acylating derivative of the acid of Formula II in an active ester of γ-benzyloxybutyric acid, and most preferably its active ester with N-hydroxysuccinimide, N-hydroxy-5-norbornene-2,3-dicarboximide or N-hydroxyphthalimide.

In a most preferred embodiment, this invention relates to the preparation of 1-N-[L-(−)-γ-amino-α-hydroxybutyryl]kanamycin A or a nontoxic pharmaceutically acceptable acid addition salt thereof, which comprises acylating polysilylated kanamycin A with a mixed acid anhydride of L-(−)-γ-benzyloxycarbonylamino-α-hydroxybutyric acid (and preferably its mixed acid anhydride with pivalic acid, benzoic acid, isobutylcarbonic acid or benzylcarbonic acid) in a substantially anhydrous organic solvent, and subsequently removing all blocking groups.

In another most preferred embodiment, this invention relates to the preparation of 1-N-[L-(−)-γ-amino-α-hydroxybutyryl]kanamycin A or a nontoxic pharmaceutically acceptable acid addition salt thereof, which comprises acylating polysilylated kanamycin A containing a carbobenzyloxy group on the 6′-amino moiety with a mixed acid anhydride of L-(−)-γ-benzyloxycarbonylamino-α-hydroxybutyric acid (and preferably its mixed acid anhydride with pivalic acid, benzoic acid, isobutylcarbonic acid or benzylcarbonic acid) in a substantially anhydrous organic solvent, and subsequently removing all blocking groups.

In another most preferred embodiment, this invention relates to the preparation of 1-N-[L-(−)-γ-amino-α-hydroxybutyryl]kanamycin A or a nontoxic pharmaceutically acceptable acid addition salt thereof, which comprises acylating polysilylated kanamycin A containing carbobenzyloxy groups on the 3-amino and 6′-amino moieties with a mixed acid anhydride of L-(−)-γ-benzyloxycarbonylamino-α-hydroxybutyric acid (and preferably its mixed acid anhydride with pivalic acid, benzoic acid, isobutylcarbonic acid or benzylcarbonic acid) in a substantially anhydrous organic solvent, and subsequently removing all blocking groups.

In another most preferred embodiment, this invention relates to the preparation of 1-N-[L-(−)-γ-amino-α-hydroxybutyryl]kanamycin A or a nontoxic pharmaceutically acceptable acid addition salt thereof, which comprises acylating polysilylated kanamycin A with an active ester of L-(−)-γ-benzyloxycarbonylamino-α-hydroxybutyric acid (and preferably its active ester with N-hydroxysuccinimide, N-hydroxy-5-norbornene-2,3-dicarboximide or N-hydroxyphthalimide) in a substantially anhydrous organic solvent, and subsequently removing all blocking groups.

In another most preferred embodiment, this invention relates to the preparation of 1-N-[L-(−)-γ-amino-α-hydroxybutyryl]kanamycin A or a nontoxic pharmaceutically acceptable acid addition salt thereof, which comprises acylating polysilylated kanamycin A containing a carbobenzyloxy group on the 6′-amino moiety with an active ester of L-(−)-γ-benzyloxycarbonylamino-α-hydroxybutyric acid (and preferably its active ester with N-hydroxysuccinimide, N-hydroxy-5-norbornene-2,3-dicarboximide or N-hydroxyphthalimide) in a substantially anhydrous organic solvent, and subsequently removing all blocking groups.

In another most preferred embodiment, this invention relates to the preparation of 1-N-[L-(−)-γ-amino-α-hydroxybutyryl]kanamycin A or a nontoxic pharmaceutically acceptable acid addition salt thereof, which comprises acylating polysilylated kanamycin A containing carbobenzyloxy groups on the 3-amino and 6′-amino moieties with an active ester of L-(−)-γ-benzyloxycarbonylamino-α-hydroxybutyric acid (and preferably its active ester with N-hydroxysuccinimide, N-hydroxy-5-norbornene-2,3-dicarboximide or N-hydroxyphthalimide) in a substantially anhydrous organic solvent, and subsequently removing all blocking groups.

In another aspect, the present invention provides polysilylated kanamycin A or B or polysilylated kanamycin A or B containing a conventional non-silyl blocking group on the 3-amino group, the 6′-amino group or the 3-amino and 6′-amino groups. In a preferred embodiment the material is polysilylated kanamycin A or B (and preferably polysilylated kanamycin A) containing an average number of silyl groups (and preferably trimethylsilyl groups) per molecule of from 4 to 8. In another preferred embodiment the material is polysilylated kanamycin A or B (and preferably polysilylated kanamycin A) containing a conventional non-silyl blocking group on the 6′-amino group and containing an average number of silyl groups (and preferably trimethylsilyl groups) per molecule of from 3 to 7. In another preferred embodiment the material is polysilylated kanamycin A or B (and preferably polysilylated kanamycin A) containing conventional non-silyl blocking groups on the 3-amino and 6′-amino groups and containing an average number of silyl groups (and preferably trimethylsilyl groups) per molecule of from 3 to 6.

When the material is polysilylated kanamycin A or B containing a non-silyl blocking group on the 3- and/or 6′-amino moiety, said blocking group is preferably selected from those of the formulae

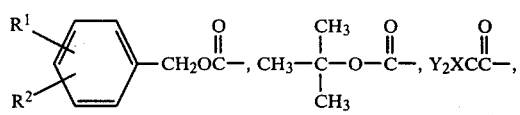

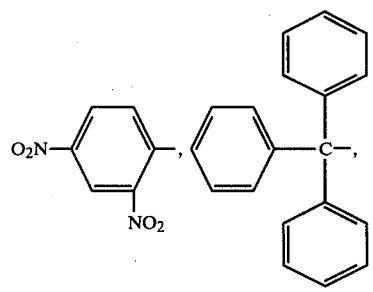

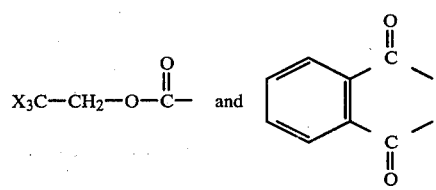

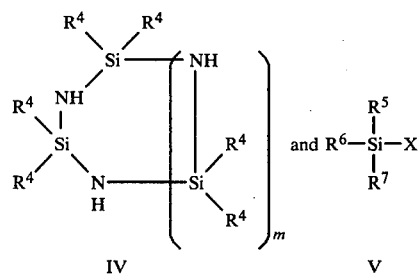

wherein $R^1$ and $R^2$ are alike or different and each is H, F, Cl, Br, $NO_2$, OH (lower)alkyl or (lower)alkoxy, X is Cl, Br, F or I, and Y is H, Cl, Br, F or I. The most preferred blocking group is the carbobenzyloxy group.

As used herein and in the claims, the term "nontoxic, pharmaceutically acceptable acid addition salt" of a compound of Formula I means a mono-, di-, tri- or tetrasalt formed by the interaction of one molecule of a compound of Formula I with 1–4 equivalents of a nontoxic, pharmaceutically acceptable acid. Included among these acids are acetic, hydrochloric, sulfuric, maleic, phosphoric, nitric, hydrobromic, ascorbic, malic and citric acid, and those other acids commonly used to make salts of amine-containing pharmaceuticals.

Acylation of the polysilylated kanamycin A or B starting material (with or without a non-silyl blocking group on the 3- and/or 6'-amino moiety) may, in general, be conducted in an organic solvent in which the starting material has sufficient solubility. These starting materials are highly soluble in most common organic solvents. Suitable solvents include for example, acetone, diethyl ketone, methyl n-propyl ketone, methyl isobutyl ketone, methyl ethyl ketone, acetonitrile, heptane, glyme, diglyme, dioxane, toluene, tetrahydrofuran, cyclohexanone, pyridine, methylene chloride, chloroform, carbon tetrachloride and mixtures of acetone/butanol or diethyl ketone/butanol. The choice of solvent is dependent on the particular starting materials employed. Ketones, generally, are the preferred solvents. The most advantageous solvent for the particular combination of reactants being utilized can readily be determined by routine experimentation.

Suitable silylating agents for use in preparing the polysilylated kanamycin starting materials utilized herein include those of the formula wherein $R^5$, $R^6$ and $R^7$ are selected from the group consisting of hydrogen, halogen, (lower)alkyl, (lower)alkoxy, halo(lower)alkyl and phenyl, at least one of the said $R^5$, $R^6$ and $R^7$ groups being other than halogen or hydrogen; $R^4$ is (lower)alkyl, m is an integer of 1 to 2 and X is selected from the group consisting of halogen and

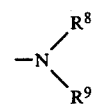

wherein $R^8$ is hydrogen or (lower)alkyl and $R^9$ is hydrogen, (lower)alkyl or

in which $R^5$, $R^6$ and $R^7$ are as defined above.

Specific silyl compounds of Formulas IV and V are: trimethylchlorosilane, hexamethyldisilazane, triethylchlorosilane, methyltrichlorosilane, dimethyldichlorosilane, triethylbromosilane, tri-n-propylchlorosilane, methyldiethylchlorosilane, dimethylethylchlorosilane, dimethyl-t-butylchlorosilane, phenyldimethylbromosilane, benzylmethylethylchlorosilane, phenylethylmethylchlorosilane, triphenylchlorosilane, triphenylfluorosilane, tri-o-tolylchlorosilane, tri-p-dimethylaminophenylchlorosilane, N-ethyltriethylsilylamine, hexaethyldisilazane, triphenylsilylamine, tri-n-propylsilylamine, tetraethyldimethyldisilazane, hexaphenyldisilazane, hexa-p-tolyldisilazane, etc. Also useful are hexaalkylcyclotrisilazanes and octa-alkylcyclotetrasilazanes. Other suitable silylating agents are silylamides (such as trialkylsilylacetamides and bis-trialkylsilylacetamides), silylureas (such as trimethylsilylurea) and silylureides. Trimethylsilylimidazole also may be utilized.

A preferred silyl group is the trimethylsilyl group and preferred silylating agents for introducing the trimethylsilyl group are hexamethyldisilazane, bis(trimethylsilyl)acetamide, trimethylsilylacetamide and trimethylchlorosilane. Hexamethyldisilazane is most preferred.

When utilizing polysilylated kanamycin A or B containing a non-silyl blocking group on the 3- and/or 6'-amino moiety as a starting material, said starting material may be prepared either by polysilylating the desired N-blocked kanamycin A or B, or by introducing the desired N-blocking group into polysilylated kanamycin A or B.

Methods for the introduction of silyl groups into organic compounds, including certain aminoglycosides, are known in the art. The polysilylated kanamycins (with or without a non-silyl blocking group on the 3- and/or 6'-amino moiety) may be prepared by methods which are known per se, or as described in this specification.

As used herein, the term polysilylated kanamycin A or B refers to kanamycin A or B containing from two to ten silyl groups in the molecule. Thus, the term polysilylated kanamycin A or B does not include persilylated kanamycin A or B, which would contain eleven silyl groups in the molecule. Similarly, polysilylated kanamycin A or B containing a single non-silyl blocking group on the 3-amino or 6'-amino moiety includes the N-blocked kanamycin containing from two to nine silyl groups (and excludes the persilylated compound which would contain ten silyl groups), while polysilylated kanamycin A or B containing non-silyl blocking groups on both the 3-amino and 6'-amino moieties includes the di-N-blocked kanamycin containing from two to eight silyl groups (and excludes the persilylated compound which would contain nine silyl groups).

The precise number of silyl groups (or their location) present in the polysilylated kanamycin starting materials (with or without a non-silyl blocking group on the 3- and/or 6'-amino moiety) is not known. We have found that both undersilylation and oversilylation lower the yield of the desired product and increase the yield of other products. In the case of gross under- or oversilylation, little or none of the desired product may be formed. The degree of silylation which will give the greatest yield of desired product will depend on the particular reactants being used in the acylation step. The most advantageous degree of silylation using any combination of reactants can readily be determined by routine experimentation.

When preparing 1-N-[L-(−)-γ-amino-α-hydroxybutyryl]kanamycin A by acylating polysilylated kanamycin A with the N-hydroxysuccinimide ester of L-(−)-γ-benzyloxycarbonylamino-α-hydroxybutyric acid in acetone solution, we have found that good yields of the desired product are obtained by utilizing polysilylated kanamycin A which has been prepared by reacting from about 4 to about 5.5 moles of hexamethyldisilazane per mole of kanamycin A. Greater or lesser amounts of hexamethyldisilazane may be utilized, but the yield of desired product in the subsequent acylation step is lowered significantly. In the specific process set forth above we prefer to utilize from about 4.5 to about 5.0 moles of hexamethyldisilazane per mole of kanamycin in order to obtain maximum yield of product in the acylation step.

It will be appreciated that each mole of hexamethyldisilazane is capable of introducing two equivalents of the trimethylsilyl group into kanamycin A or B. Kanamycin A and B each have a total of eleven sites (NH$_2$ and OH groups) which might be silylated, while kanamycin A and B containing a non-silyl blocking group on the 3-amino or 6'-amino moiety each have a total of 10 such sites, and kanamycin A and B containing non-silyl blocking groups on both the 3-amino and 6'-amino moieties each contain 9 such sites. Thus, 5.5 moles of hexamethyldisilazane per mole of kanamycin A or B could theoretically completely silylate all OH and NH$_2$ moieties of the kanamycin, while 5.0 moles of hexamethyldisilazane could completely silylate one mole of kanamycin A or B containing a single non-silyl blocking group, and 4.5 moles of hexamethyldisilazane could completely silylate one mole of kanamycin A or B containing two non-silyl blocking groups. However, we believe that such extensive silylation does not take place with these molar ratios during reasonable reaction time periods, although higher degrees of silylation are obtained in a given reaction time when a silylation catalyst is added.

Silylation catalysts greatly accelerate the rate of silylation. Suitable silylation catalysts are well known in the art and include inter alia amine sulfates (e.g. kanamycin sulfate), sulfamic acid, imidazole and trimethylchlorosilane. Silylation catalysts generally promote a higher degree of silylation than is required in the process of this invention. However, oversilylated kanamycin A or B can be used as starting material if it is first treated with a desilylating agent to reduce the degree of silylation before the acylation reaction is carried out.

Good yields of desired product are obtained when acylating polysilylated kanamycin A prepared using a 5.5:1 molar ratio of hexamethyldisilazane to kanamycin A. However, when kanamycin A silylated with a 7:1 molar ratio of hexamethyldisilazane (or with a 5.5:1 molar ratio in the presence of a silylation catalyst) was acylated in acetone with the N-hydroxysuccinimide ester of L-(−)-γ-benzyloxycarbonylamino-α-hydroxybutyric acid, less than a 1% yield of the desired product was obtained. However, when this same "oversilylated" kanamycin A was acylated with the same acylating agent in acetone solution to which water [21 moles water per mole of kanamycin; 2.5% water (W/V)] had been added as a desilylating agent 1 hour before acylation, a yield of approximately 40% of the desired product was obtained. The same results are obtained if the water is replaced by methanol or other active hydrogen compound capable of effecting desilylation, e.g. ethanol, propanol, butanediol, methyl mercaptan, ethyl mercaptan, phenyl mercaptan, or the like.

Although it is usual to utilize dry solvents when working with silylated materials, we have surprisingly found that, even in the absence of "oversilylation", the addition of water to the reaction solvent prior to acylation often gives equally good yields, and sometimes gives better yields of desired product than in a dry solvent. In acylation reactions conducted in acetone at the usual concentrations of 10–20% (W/V) of polysilylated kanamycin A, we have found that excellent yields of 1-N-[L-(−)-γ-amino-α-hydroxybutyryl]kanamycin A were obtained when adding up to 28 moles of water per mole of polysilylated kanamycin A; at 20% concentration, 28 moles per mole is approximately 8% water. With other combinations of reactants and solvents, even more water may be tolerated or be beneficial. The acylation reaction may be conducted in solvents containing up to about 40% water, although at such high water concentrations one must utilize short acylation times in order to avoid excessive desilylation of the polysilylated kanamycin A or B starting material. Accordingly, as used herein and in the claims, the term "substantially anhydrous organic solvent" is intended to include solvents containing up to about 40% water. A preferred range is up to about 20% water, a more preferred range is up to about 8% water and the most preferred range is up to about 4% water.

As indicated above, the most desirable degree of silylation for any combination of acylation reactants may be readily determined by routine experimentation.

It is believed that the preferred average number of silyl groups in the starting material will usually be between 4 and 8 for kanamycin A or B, between 3 and 7 for kanamycin A or B containing a single non-silyl blocking group and between 3 and 6 for kanamycin A or B containing two non-silyl blocking groups, but this is only theory and is not considered an essential part of this invention.

Except as described above for solvents containing very high water levels, the duration of the acylation reaction is not critical. Temperatures in the range of about −30° C. to about 100° C. may be used for reaction times ranging from about one hour up to a day or more. The reaction usually proceeds well at room temperature and, for convenience, may be conducted at ambient temperature. However, for maximum yields and selective acylation, we prefer to conduct the acylation at from about 0° to 5°.

Acylation of the 1-amino moiety of the polysilylated kanamycin A or B (with or without a non-silyl blocking group on the 3- and/or 6'-amino moiety) may be conducted with any acylating derivative of the acid of Formula II which is known in the art to be suitable for the acylation of a primary amino group. Examples of suitable acylating derivatives of the free acid include the corresponding acid anhydrides, mixed anhydrides, e.g. alkoxyformic anhydrides, acid halides, acid azides, active esters and active thioesters. The free acid may be coupled with the polysilylated kanamycin starting material after first reacting said free acid with N,N'-dimethylchloroformininium chloride [cf. Great Britain No. 1,008,170 and Novak and Weichet, Experientia XXI, 6, 360 (1965)] or by the use of an N,N'-carboxyldiimidazole or an N,N'-carbonyldtriazole [cf. South African Specification No. 63/2684] or a carbodiimide reagent [especially N,N'-dicyclohexylcarbodiimide, N,N'-diisopropylcarbodiimide or N-cyclohexyl-N'-(2-morpholinoethyl)carbodiimide: cf. Sheehan and Hess, J.A.C.S., 77, 1967 (1955)], or of an alkynylamine reagent [cf. R. Buijle and H. G. Viehe, Angew. Chem. International Edition, 3, 582, (1964)] or of an isoxazolium salt reagent [cf. R. B. Woodward, R. A. Olofson and H. Mayer, J. Amer. Chem. Soc., 83, 1010 (1961)], or of a ketenimine reagent [cf. C. L. Stevens and M. E. Munk, J. Amer. Chem. Soc., 80, 4065 (1958)] or of hexachlorocyclotriphosphatriazine or hexabromocyclotriphosphatriazine (U.S. Pat. No. 3,651,050) or of diphenylphosphoryl azide [DDPA; J. Amer. Chem. Soc., 94, 6203–6205 (1972)] or of diethylphosphoryl cyanide [DEPC; Tetrahedron Letters No. 18, pp. 1595–1598 (1973)] or of diphenyl phosphite [Tetrahedron Letters No. 49, pp. 5047–5050 (1972)]. Another equivalent of the acid is a corresponding azolide, i.e., an amide of the corresponding acid whose amide nitrogen is a member of a quasiaromatic five membered ring containing at least two nitrogen atoms, i.e., imidazole, pyrazole, the triazoles, benzimidazole, benzotriazole and their substituted derivatives. As will be appreciated by those skilled in the art, it sometimes may be desirable or necessary to protect the hydroxyl group of the acylating derivative of the acid of Formula II, e.g. when utilizing acylating derivatives such as an acid halide. Protection of the hydroxyl group may be accomplished by means known in the art, e.g. by use of a carbobenzyloxy group, by acetylation, by silylation, or the like.

After completion of the acylation reaction, all blocking groups are removed by methods known per se to yield the desired product of Formula I. The silyl groups may, for example, readily be removed by hydrolysis with water, preferably at low pH. Blocking group B of the acylating derivatives of the acid of Formula II, and the blocking group on the 3- and/or 6'-amino moiety of the polysilylated kanamycin starting material (if present) may also be removed by known methods. Thus, a t-butoxycarbonyl group may be removed by the use of formic acid, a carbobenzyloxy group by catalytic hydrogenation, a 2-hydroxy-1-naphthcarbonyl group by acid hydrolysis, a trichloroethoxycarbonyl group by treatment with zinc dust in glacial acetic acid, the phthaloyl group by treatment with hydrazine hydrate in ethanol under heating, the trifluoroacetyl group by treatment with $NH_4OH$, etc..

Yields of product were determined by various methods. After removal of all blocking groups and chromatography on a CG-50 ($NH_4+$) column, the yield of BB-K8 could be determined by isolation of the crystalline solid from the appropriate fractions or by microbiological assay (turbidimetric or plate) of the appropriate fractions. Another technique which we utilized was high performance liquid chromatography of the unreduced acylation mixture, i.e. the aqueous solution obtained after hydrolysis of the silyl groups and removal of organic solvent but before hydrogenolysis to remove the remaining blocking group(s). This assay was not a direct assay for BB-K8 or BB-K29, but for the corresponding mono- or di-N-blocked compounds.

The instrument utilized was a Waters Associates ALC/GPC 244 high pressure liquid chromatograph with a Waters Associates Model 440 absorbance detector and a 30 cm × 3.9 mm i.d. μ-Bondapak C-18 column, under the following conditions:

| | |
|---|---|
| Mobile Phase | 25% 2-propanol |
| | 75% 0.01M sodium acetate pH 4.0 |
| Flow Rate | 1 ml./minute |
| Detector | UV at 254 nm. |
| Sensitivity | 0.04 AUFS |
| Diluent | DMSO |
| Injected Amount | 5 μl |
| Concentration | 10 mg./ml. |

Chart speed varied, but 2 minutes/inch was typical. The above conditions gave UV traces with peaks which were easy to measure quantitatively. The results of the above analyses are referred to in the specification as HPLC assays.

In order to avoid the repetition of complex chemical names, the following abbreviations are sometimes utilized in this specification.

| | |
|---|---|
| AHBA | L-(−)-γ-amino-α-hydroxybutyric acid |
| BHBA | N—Carbobenzyloxy derivative of AHBA |
| HONB | N—hydroxy-5-norbornene-2,3-dicarboximide |
| NAE (or BHBA—'ONB') | N—hydroxy-5-norbornene-2,3-dicarboximide activated ester of BHBA |
| HONS | N—hydroxysuccinimide |
| SAE (or BHBA—'ONS') | N—hydroxysuccinimide activated ester of BHBA |
| DCC | dicyclohexylcarbodiimide |
| DCU | dicyclohexylurea |
| HMDS | hexamethyldisilazane |
| BSA | bis(trimethylsilyl)acetamide |
| MSA | trimethylsilylacetamide |
| TFA | trifluoroacetyl |
| t-BOC | tert. butyloxycarbonyl |

"Dicalite" is a trademark of the Great Lakes Carbon Corporation for diatomaceous earth.

"Amberlite CG-50" is a Tademark of the Rohm & Haas Co. for the chromatographic grade of a weakly acid cationic exchange resin of the carboxylic-polymethacrylic type.

"μ-Bondapak" is a Trademark of Waters Associates for a series of high performance liquid chromatography columns.

All temperatures herein are given in degrees centigrade. As used herein, the terms "(lower)alkyl" and "(lower)alkoxy" refer to alkyl or alkoxy groups containing from 1 to six carbon atoms.

DESCRIPTION OF THE PREFERRED EMBODIMENTS

EXAMPLE 1

Preparation of
1-N-[L-(−)-γ-Amino-α-hydroxybutyryl]kanamycin A (BB-K8) by Selective Acylation of Poly(trimethylsilyl) 6'-N-Carbobenzyloxykanamycin A in Anhydrous Diethyl Ketone 6'-N-Carbobenzyloxykanamycin A (15 g., 24.24 m. moles) was slurred in 90 ml. of dry acetonitrile and heated to reflux under a nitrogen atmosphere. Hexamethyldisilazane (17.5 g., 108.48 m. moles) was added slowly over 30 minutes, and the resulting solution was refluxed for 24 hours. After removal of the solvent in vacuo (40°) and complete drying under vacuum (10 mm), 27.9 g. of a white, amorphous solid was obtained [90.71% calculated as 6'-N-Carbobenzyloxykanamycin A (Silyl)$_9$].

This solid was dissolved in 150 ml. of dry diethyl ketone at 23°. L-(−)-γ-benzyloxycarbonylamino-α-hydroxybutyric acid N-hydroxy-5-norbornene-2,3-dicarboximide ester (NAE) (11.05 g., 26.67 m. moles) dissolved in 100 ml. of dry diethyl ketone at 23° was added slowly with good agitation over ½ hour. The solution was stirred at 23° for 78 hours. The yellow, clear solution (pH 7.0) was diluted with 100 ml. of water. The pH of the mixture was adjusted to 2.8 (3 N HCl) and stirred vigorously at 23° for 15 minutes. The aqueous phase was separated, and the organic phase was extracted with 50 ml. of pH 2.8 water. The combined aqueous fractions were washed with 50 ml. of ethyl acetate. The solution was placed in a 500 ml. Parr bottle, together with 5 g. of 5% palladium on carbon catalyst (Engelhard) and reduced at 50 psi H$_2$ for 2 hours at 23°. The mixture was filtered through a pad of Dicalite which was then washed with an additional 30 ml. of water. The colorless filtrate was concentrated in vacuo (40°–45°) to 50 ml. The solution was charged on a 5×100 cm CG-50 (NH$_4$+) ion exchange column. After washing with 1000 ml. of water, unreacted kanamycin A, 3-[L-(−)-γ-amino-α-hydroxybutyryl]kanamycin A (BB-K29) and BB-K8 were eluted with 0.5 N ammonium hydroxide. Polyacyl material was recovered with 3 N ammonium hydroxide. Bioassay, thin layer chromatography and optical rotation were used to monitor the progress of elution. The volume and observed optical rotation of each fraction of eluate, as well as the weight and percent yield of solid isolated from each fraction by evaporation to dryness, are summarized below:

| Material | Volume (ml) | α$_{578}$ | Weight (gms.) | % Yield |
|---|---|---|---|---|
| Kanamycin A | 1000 | +0.115 | 0.989 | 9.15 |

-continued

| Material | Volume (ml) | α$_{578}$ | Weight (gms.) | % Yield |
|---|---|---|---|---|
| BB-K29 | 1750 | +0.24 | 4.37 | 32.0 |
| BB-K8 | 2000 | +0.31 | 6.20 | 47.4 |
| Polyacyls | 900 | +0.032 | 0.288 | 2.0 |

The spent diethyl ketone layer was shown by high performance liquid chromatography to contain an additional 3–5% BB-K8.

The crude BB-K8 (6.20 gms.) was dissolved in 20 ml. of water and diluted with 20 ml of methanol, and 20 ml. of isopropanol was added to induce crystallization. There was obtained 6.0 gms. (45.8%) of crystalline BB-K8.

EXAMPLE 2

Preparation of
1-N-[L-(−)-γ-Amino-α-hydroxybutyryl]kanamycin A (BB-K8) by Selective Acylation of Poly(trimethylsilyl) 6'-N-Carbobenzyloxykanamycin A in Anhydrous Acetone Poly(trimethylsilyl) 6'-N-carbobenzyloxy kana A prepared as in Example 1 (103 g., 0.081 moles, calculated as 6'-N-Carbobenzyloxykanamycin A (Silyl)$_9$) was dissolved in 100 ml. of dry acetone at 23°. L-(−)-γ-benzyloxycarbonylamino-α-hydroxybutyric acid N-hydroxy-5-norbornene-2,3-dicarboximide ester (NAE) (35.24 g., 0.085 moles) dissolved in 180 ml. of dry acetone at 23° was added slowly with good agitation to the solution of poly(trimethylsilyl) 6'-N-Carbobenzyloxykanamycin A over a 15 minute period. The solution was stirred at 23° for 20 hours under a nitrogen atmosphere. The pale yellow, clear solution (pH 7.2) was diluted with 100 ml. of water. The pH of the mixture was adjusted to 2.5 (3 N HCl) and stirring continued at 23° for 15 minutes. Acetone was removed using steam-ejector vacuum at about 35°. The solution was placed in a 500 ml. Parr bottle, together with 10 g. of 5% palladium on carbon catalyst (Engelhard) and reduced at 40 psi H$_2$ for 2 hours at 23°. The mixture was filtered through a pad of diatomaceous earth which was then washed with an additional 50 ml. of water. After concentration to approximately ⅓ volume, the solution (pH 6.0–7.2) was charged on a 6×110 cm. CG-50 (NH$_4$+) ion exchange column and eluted with a stepwise gradient from H$_2$O to 0.6 N ammonium hydroxide to recover BB-K8. An automatic polarimeter was used to monitor the progress of elution. Combinations were made on the basis of thin layer chromatography evaluation. the combined BB-K8 fractions were concentrated to 25–30% solids. The solution was diluted with an equal volume of methanol, followed by two volumes of isopropanol to induce crystallization. There was recovered 18.2 g. (40%) of crystalline BB-K8.

The recovery of 12% kanamycin A, 40% BB-K29 and 5% polyacylated kanamycin gave a material balance of 97%.

EXAMPLE 3

Preparation of 1-N-[L-(−)-γ-Amino-α-hydroxybutyryl]kanamycin A (BB-K8) by Selective Acylation of Poly(trimethylsilyl) Kanamycin A, Using In Situ Blocking

A. Poly(trimethylsilyl) Kanamycin A

Kanamycin A free base (18 g. activity, 37.15 m. moles) was slurried in 200 ml. of dry acetonitrile and heated to reflux. Hexamethyldisilazane (29.8 g., 184.6 m. moles) was added over 30 minutes and the mixture was stirred at reflux for 78 hours to give a light yellow clear solution. Removal of the solvent under vacuum left an amorphous solid residue (43 gm., 94%) [calculated as kanamycin A (silyl)$_{10}$].

B. 1-N-[L-(−)-γ-Amino-α-hydroxybutyryl]kanamycin A p-(Benzyloxycarbonyloxy)benzoic acid (5.56 g., 20.43 m. moles) was slurried in 50 ml. of dry acetonitrile at 23°. N,O-bis-Trimethylsilyl acetamide (8.4 g., 41.37 m. mole) was added with good stirring. The solution was held for 30 minutes at 23°, and then added over 3 hours with vigorous stirring to a solution of poly(trimethylsilyl)kanamycin A (21.5 g., 17.83 m. mole, calculated as the (silyl)$_{10}$ compound) in 75 ml. of dry acetonitrile at 23°. The mix was stirred for 4 hours, the solvent was removed in vacuo (40°), and the oily residue was dissolved in 50 ml. of dry acetone at 23° C.

L-(−)-γ-benzyloxycarbonylamino-α-hydroxybutyric acid N-hydroxy-5-norbornene-2,3-dicarboximide ester (NAE) (8.55 g., 20.63 m. moles) in 30 ml. of acetone was added to the above solution over a period of 5 minutes. The mixture was held at 23° C. for 78 hours. The solution was diluted with 100 ml. of water and the pH (7.0) lowered to 2.5 (6 N HCl). The mixture was placed in a 500 ml. Parr bottle together with 3 g. of 5% palladium on carbon catalyst (Engelhard) and reduced at 40 psi H$_2$ for 2 hours at 23°. The mixture was filtered through a pad of diatomaceous earth which was then washed with 20 ml. of water. The combined filtrate and washings (168 ml.) were determined by microbiological assay against *E. coli* to contain approximately 11,400 mcg/ml. (19% yield) of BB-K8.

EXAMPLE 4

Preparation of 1-N-[L-(−)-γ-Amino-α-hydroxybutyryl]kanamycin A (BB-K8) by Selective Acylation of Poly(trimethylsilyl)Kanamycin A

A. Poly(trimethylsilyl) Kanamycin A

A suspension of 10 g. (20.6 m. moles) kanamycin A in 100 ml. of dry acetonitrile and 25 ml. (119 m. moles) 1,1,1,3,3,3-hexamethyldisilazane was refluxed for 72 hours. A clear light yellow solution resulted. The solution was stripped to dryness in vacuo at 30°–40° C. There was obtained 21.3 g. of poly(trimethylsilyl) Kanamycin A as a light tan amorphous powder [85% yield calculated as kanamycin A (silyl)$_{10}$].

B. 1-N-[L-(−)-γ-Amino-α-hydroxybutyryl]kanamycin A

To a solution of 2.4 g. (2.0 m. moles) of poly(trimethylsilyl) Kanamycin A in 30 ml. of dry acetone was added slowly 2.0 m. moles of L-(−)-γ-benzyloxycarbonylamino-α-hydroxybutyric acid N-hydroxy-5-norbornene-2,3-dicarboximide ester (NAE) in 10 ml. of dry acetone at 0°–5° C. The reaction mixture was stirred at 23° C. for a week and then stripped to dryness in vacuo at a bath temperature of 30°–40° C. Water (60 ml.) was then added to the residue, followed by 70 ml. of methanol to obtain a solution. The solution was acidified with 3 N HCl to pH 2.0 and then reduced at 50 psi H$_2$ for 2 hours, using 500 mg of 5% palladium on carbon catalyst. The material was filtered, and the combined filtrate and washings were determined by microbiological assay against *E. coli* to contain a 29.4% yield of BB-K8.

EXAMPLE 5

Preparation of BB-K8 by Selective N-Acylation of Polytrimethylsilyl 6'-N-Carbobenzoxy Kanamycin A in Anhydrous Acetone

I. Summary

Silylation of 6'-N-carbobenzoxy Kana A in acetonitrile using hexamethyldisilazane (HMDS) affords the 6'-N-carbobenzoxy Kana A (silyl)$_9$ intermediate ①. This silylated Kana A is readily soluble in most organic solvents. Acylation with NAE in anhydrous acetone at 23° using a 5% molar excess of NAE relative to 6'-N-Cbz Kana A input afforded a mixture containing only Cbz derivatives of BB-K8 and BB-K29, some unreacted Kana A and some polyacyl material. No BB-K11 was detectable in any of these studies. Elution of an acetone acylation mix, after reduction and workup, from a CG-50 (NH$_4$+) column using an ammonium hydroxide gradient afforded isolated yields of pure BB-K8 in the 40% range.

II. Equations

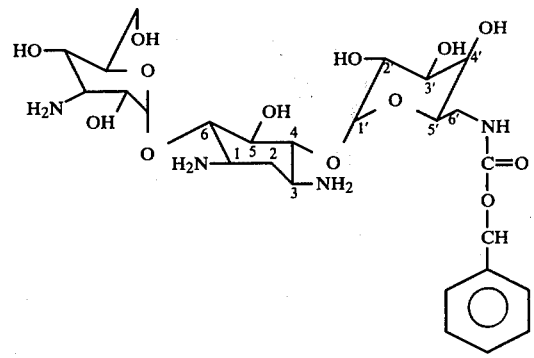

6'-N—Cbz Kana A
C$_{26}$H$_{42}$O$_{13}$N$_4$ (618.65)

+ (CH$_3$)$_3$Si—NH—Si(CH$_3$)$_3$

HMDS (161.4)

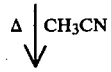

-continued

RO, OR, RHN, OR, OH, RHN, NHR, O, NH, C=O, +NH3, CH, phenyl (structure diagram)

R = Si(CH3)3
1  6'-N—Cbz Kana A (Silyl)9
   C53H114O13N4Si9 (1268.3)

B.

CbzNH(CH2)2—CH(OH)—COOH + HON(norbornene dicarboximide) + DCC

BHBA (253.4)        HONB (179.2)        (206)

↓ Acetone

DCU + CbzHN(CH2)2—CH(OH)—C(O)—O—N(norbornene dicarboximide)

(224.3)

2  NAE (414.6)

C.

1 + 2 →(Acetone, 23°)→ { diCbzBB-K8 (854) + diCbzBB-K29 + 6'Cbz-1,3-diBHBA-Kana A + 6'Cbz Kana A }

↓ H2 / 5% Pd/C

BB-K8 + BB-K29 + 1,3-diAHBA-Kana A + Kana A (585.62)    (722.76)           (484.5)

↓ CG-50(NH4+)

BB-K8

III. Materials

|  | Wgt. g. | Vol. ml. | Moles |
|---|---|---|---|
| 6'-N—Cbz Kana A | 50 |  | .081 |
| HMDS | 58.9 | 76.5 | .365 |
| Acetonitrile |  | 300 |  |
| BHBA | 21.5 |  | .085 |
| HONB | 15.2 |  | .085 |
| DCC | 17.48 |  | .085 |
| Acetone |  | 260 |  |
| CG-50(NH4+) |  | 3000 |  |
| Methanol |  | As required |  |
| IPA |  | As required |  |

IV. Safety

| | |
|---|---|
| 6'-N—Cbz Kana A | No direct information available. Avoid dust contact. |
| Acetonitrile | Treat as a cyanide. Avoid breathing vapors. May cause skin irritation. |
| Hexamethyldisilazane (HMDS) | Irritant, handle with care. |
| 6'-N—Cbz Kana A (Silyl)9 | No direct information available, handle with care. |
| BHBA | Toxicity is not established. Avoid exposure to solids. |
| HONB | Toxicity unknown. Use precaution in handling. |
| DCC | A severe skin and eye irritant. Avoid inhalation of mist or vapors. Toxic. |
| Acetone | Flammable. Inhalation may produce headache, fatigue, excitement, bronchial irritation, and, in large amounts narcosis. |
| NAE | No direct information available; always handled directly as solution in acetone. |
| Methanol | Flammable. Poisoning may occur from ingestion, inhalation or percutaneous absorption. |
| Isopropanol | Flammable. Ingestion or inhalation of large quantities of the vapor may cause headache, dizziness, mental depression, vomiting, narcosis. |
| Ammonium hydroxide | Toxic vapors. Wear mask, avoid contact with liquid. |
| CG-50(NH4+) | No toxicity data available, handle with care. |

V. Procedure

A. Preparation 6'-N-Carbobenzyloxykanamycin A (silyl)9 [6'-N-Cbz Kana A (Silyl)9]

1. Slurry 50 g. of 6'-N-carbobenzyloxykanamycin A (KF<4%) in 300 ml. of acetonitrile (KF<0.01%). Bring to reflux (74°) maintaining a stream of dry nitrogen through the slurry.

2. Add slowly over a 30 minute period 75.8 ml. hexamethyldisilazane (HMDS). Complete solution will occur with evolution of ammonia gas.

3. Continue refluxing for 18–20 hours under a nitrogen purge.

4. Concentrate the clear, light yellow solution under vacuum (bath temp. 40°–50°) to a foamy solid. Yields of the silyl9 compound 89–92 g. (90–94% Theory).

NOTE: For future reference; in other solvent studies this solid is normally not isolated but used directly for the acylation.

B. Preparation of N-hydroxy-5-norbornene-2,3-dicarboximide ester of L-(—)-α-carbobenzyloxyamino-α-hydroxybutyric acid (NAE)

1. Dissolve 21.5 g. of L-(—)-γ-carbobenzyloxyamino-α-hydroxybutyric acid (BHBA) in 100 ml. of dry acetone at 23° followed by 15.2 g. of N-hydroxy-5-norbornene-2,3-dicarboximide (HONB). A complete solution will result.

2. Over 30 minutes add a solution of 17.48 g. of dicyclohexylcarbodiimide (DCC) in 50 ml. of acetone with agitation. The temperature will rise to approximately 40° during the addition with precipitation of dicyclohexylurea (DCU).

3. Agitate the slurry for 3–4 hours allowing the temperature to equilibrate to 23°–25°.

4. Remove the urea derivative by filtration; wash the cake with 30 ml. acetone. Save the filtrate plus washings for the acylation step below.

C. Acylation of C′-N-Cbz Kana A (Silyl)$_9$

1. Dissolve the 6′-N-Cbz Kana A (silyl)$_9$ isolated in Part A, Step 4 in 100 ml of dry acetone at 23°–24°.

2. With good agitation slowly add the NAE solution prepared in Part B over a 15 minute period. The temperature will gradually rise to approximately 40°. Allow the solution to equilibrate to 23° and continue stirring for 18–20 hours under a nitrogen atmosphere.

3. Add 100 ml. of water and lower the pH (6.9–7.2) to 2.2–2.5 with 6 N hydrochloric acid. Agitate for 15 minutes at 23°. (NOTE: A second layer may form—this does not present a problem in the workup).

4. Remove acetone under vacuum at a bath temperature of 30°–35°. Transfer the concentrate to a suitable hydrogenation vessel (prepurged with nitrogen). Add 10 g. 5% palladium on carbon catalyst, and hydrogenate at 40 psi for 2–3 hours.

5. Filter the mixture through a Dicalite pad, washing the hydrogenation vessel and cake with an additional 50 ml. water.

6. Concentrate the filtrate plus wash to approximately ⅓ volume (50 ml.) under vacuum at 40°–45°.

7. Check the pH. It should be in the range 6.9–7.2. If not, adjust with 1 N ammonium hydroxide. Charge the mixture on a CG-50 (NH$_4$+) column (6×110 cm).

8. Wash the column with 1000 ml. of deionized water. Then elute with 0.5–0.6 N ammonium hydroxide using an automatic polarimeter to monitor the progress of elution. The order of elution is as follows:

Residual Kana A→BB-K29→BB-K8.

No BB-K11 was detected in any of our acylation workups. Polyacyl material i.e. the 1,3-diAHBA analog of Kana A, is recovered by washing the column with 3 N ammonium hydroxide.

9. Combine the BB-K8 fractions and concentrate to 25–30% solids. Dilute with 1 volume of methanol, and seed with BB-K8 crystals.

10. Add slowly over 2 hours 2 volumes of isopropanol (IPA) with good stirring, and crystallize at 23° for 6–8 hours.

11. Filter the solid, wash with 50 ml. of 1:1:2 water/methanol/IPA mixture, and finally with 25 ml. IPA.

12. Dry in a vacuum over at 40° for 12–16 hours. Yield: 17.3–19.0 g. (38–42%) of BB-K8 having the following properties:

TLC

CHCl$_3$-methanol-NH$_4$OH-water (1:4:2:1), 5×20 cm. silica gel plates from Quantum Industries—one zone as detected with ninhydrin (RF ~0.4).

| Specific Rotation | | | |
|---|---|---|---|
| [α] 23° 589 C = 1.0% | H$_2$O + 101.6 | 0.1M NH$_4$OH + 101.9 | 0.1M H$_2$SO$_4$ + 103.5 |

13. The recovery of BB-K29 in this system was also 39–42%, residual Kana A 10–14% and 1,3-di AHBA-Kana A approximately 5% to give a material balance >95%.

EXAMPLE 6

Preparation of BBK8 by Selective N-Acylation of Polytrimethylsilyl Kana A in Anhydrous Acetone

I. Summary

Silylation of Kana A 'base' acetonitrile using hexamethyldisilazane (HMDS) yielded polytrimethylsilyl Kana A. The extent of silylation is as yet uncertain, but for the time being is assumed to be Kana A (Silyl)$_{10}$. Polysilylated Kana A is readily soluble in most organic solvents. Acylation with SAE in anhydrous acetone at 23° using a 1:1 molar ratio of SAE relative to Kana A input afforded a mixture containing Cbz derivatives of BBK8 and BBK29, usually in the ratio 2-3/1; BBK6 (approximately 5–8%), unreacted Kana A (15–20%) and some polyacyl material (approximately 5–10%). Again, as was seen in our previous work on the acylation of polytrimethylsilyl 6′-N-Carbobenzoxy Kana A, no BBK11 was detected in any of these experiments. Reduction and work-up of an acetone acylation mix, followed by chromatography on a CG-50-(NH$_4$+) column using 0.5 N ammonium hydroxide, afforded isolated crystalline BBK8 in the 34–39% range.

II. Equations

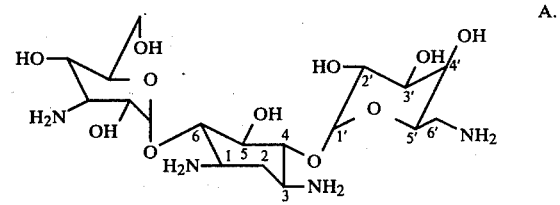

Kana A 'base'
C$_{18}$H$_{36}$O$_{11}$N$_4$ (484.51)
+ (CH$_3$)$_3$Si—NH—Si(CH$_3$)$_3$
HMDS (161.4)

Δ | CH$_3$CN

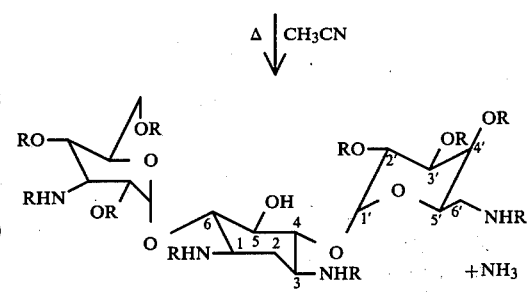

R = Si(CH$_3$)$_3$
1 Kana A (Silyl)$_{10}$
C$_{48}$H$_{116}$O$_{11}$N$_4$Si$_{10}$ (1206.35)

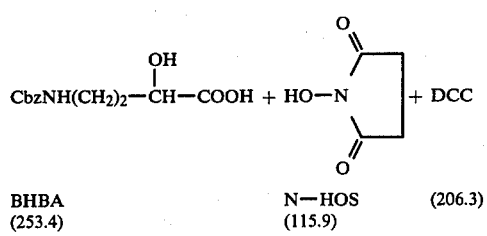

BHBA (253.4)         N—HOS (115.9)         (206.3)

EtOAc

-continued

DCU + CbzNH(CH$_2$)$_2$CH(OH)—C(=O)—O—N(succinimide)

(224.3)

2 SAE
(350.33)

$$1 + 2 \xrightarrow{\text{Acetone}}_{23°} \begin{Bmatrix} \text{Cbz BB-K8} \\ (720) \\ + \\ \text{Cbz BB-K29} \\ + \\ \text{Cbz BB-K6} \\ + \\ \text{Kana A} \\ + \\ \text{Polyacyls (Primarily 1,3-diBHBA-Kana A)} \end{Bmatrix}$$

$\xrightarrow{\text{H}_2}_{5\% \text{ Pd/C}}$

BB-K8 + BB-K29 + BB-K6 + 1,3-diAHBA-Kana A + Kana A
(585.62)                                  (722.76)

$\downarrow$ CG-50(NH$_4^+$)

BB-K8

III. Materials

|  | Wgt. g. | Vol., ml. | Moles |
|---|---|---|---|
| Kana A 'base' | 50 |  | .103 |
| HMDS (Sp. gr. 0.774) | 86.68 | 112 | .537 |
| Acetonitrile |  | 600 |  |
| SAE | 35.03 |  | .10 |
| Acetone |  | 850 |  |
| CG-50(NH$_4^\oplus$) |  | 3000 |  |
| Methanol |  | As required |  |
| IPA |  | As required |  |

IV. Safety

| Kana A 'base' | Known drug - usual caution advised. |
|---|---|
| Kana A (Silyl)$_{10}$ | No direct information available, handle with care. |
| Other materials | See Example 5 |

V. Procedure

A. Preparation of Kana A (Silyl)$_{10}$

1. Slurry 50 g. of Kana A 'base' (KF 2.5-3.5%) in 500 ml. of acetonitrile (KF <0.01%). Bring to reflux (74°) maintaining a stream of dry nitrogen through the slurry.

2. Add slowly over a 30 minute period 112 ml. hexamethyldisilazane (HMDS). Complete solution will occur within 4-5 hours with evolution of ammonia gas.

3. Continue refluxing for 22-26 hours under a nitrogen purge.

4. Concentrate the clear faint yellow solution under vacuum (40°) to a syrupy residue. Flush with an additional 100 ml. acetonitrile, and dry completely under high vacuum for 3-6 hours. Yields of whitish amorphous solid are 109-115 g. (90-95% of theory, calculated as Kana A (Silyl)$_{10}$).

B. Preparation of N-Hydroxysuccinimide ester of L-(−)-α-carbobenzyloxyamino-α-hydroxybutyric acid (SAE)

1. Dissolve 100 g of L(−)-α-benzyloxycarbonylamino-α-hydroxybutyric acid (BHBA) and 45.38 g of N-hydroxysuccinimide (N-HOS) in 1300 ml of ethyl acetate (KF<0.05%) with stirring at 23° C.

2. Dissolve 81.29 g of dicyclohexylcarbodiimide (DCC) in 400 ml. of ethyl acetate (KF<0.05%) at 23° C. With good agitation add this solution over 30 minutes to step 1 solution. The temperature will rise to ~40°-42° C. with concurrent precipitation of dicyclohexylurea (DCU). Agitate the slurry 3-4 hours allowing the temperature to equilibrate to 23° C.

3. Filter the DCU; wash the cake with 250 ml. of ethyl acetate (KF<0.05%). Discard the DCU cake. Save the filtrate and washes.

4. Concentrate the filtrate plus washes to ~500 ml. (in vacuo at 30°-35° C.). Some product will crystallize out.

5. Transfer the concentrate to a suitable vessel and add with vigorous agitation 100 ml. of heptane. If necessary, add seed crystals of SAE. Crystallization will begin almost immediately. Agitate the slurry for 30 minutes at 23° C.

6. Add, over 30 minutes, 400 ml. of heptane and agitate the slurry 4-5 hours at 23° C.

7. Filter and wash the cake with 200 ml. of 3:1 heptane/ethyl acetate following by 100 ml. of heptane.

8. Dry in a vacuum oven at 30°-35° C. for 18-20 hours.

Yield is 110.1-131.4 g (80-95%).

MP—119°-120° with softening at 114° (Corr.).

TLC—4 acetone:12 benzene:1 CH$_3$CO$_2$H—Detection 1% aqueous KMO$_4$.

Rf—0.7 for SAE; 0.2 BHBA on 2×10 cm prescored silica gel plates from Analtech Inc.

C. Acylation of Kana A (Silyl)$_{10}$

1. Dissolve the Kana A (Silyl)$_{10}$ isolated in Part A, Step 4 in 500 ml. dry acetone at 23° C.

2. With good agitation add rapidly the SAE prepared in Part B (35.03 g) as a 10% solution in dry acetone over a 5-10 minute period. The temperature will rise approximately 5°. Allow the solution to equilibrate to 23°, and continue stirring for 18-20 hours.

3. The light orange, clear solution is diluted with 400 ml. of water, and the pH (7.0-7.5) lowered to 2.2-2.5 with 3 N hydrochloric acid. The clear solution is now agitated at 23° for 15-30 minutes.

4. Acetone is removed under vacuum at a bath temperature of 30°-35° (a small amount of material may separate at this point, but presents no problem). Transfer the concentrate to a suitable hydrogenation vessel. Add 10 g 5% palladium on carbon catalyst, and hydrogenate at 50 psi for 2-3 hours.

5. Filter the mixture through a Dicalite pad, and wash the hydrogenation vessel and cake with an additional 2×50 ml. water.

6. Concentrate the filtrate plus washings to approximately $\frac{1}{3}$ volume (150-165 ml.) under vacuum at 40°-45°.

7. The pH at this point is in the range 6.0-7.0. The mixture is charged on a CG-50(NH$_4$+) column (6×110 cm).

8. Wash the column with 1000 ml. of deionized water. Elute with 0.5 N ammonium hydroxide using an automatic polarimeter to monitor the progress of elution. The order of elution is as follows:

Residual Kana A→BB-K6→BB-K29→BB-K8.

No BB-K11 was detected in any of our experiments.

9. Combine the BB-K8 fractions and concentrate to 25–30% solids. Dilute with 1 volume methanol, and seed with BB-K8 crystals.

10. Add slowly over 2 hours 2 volumes of IPA with good stirring and crystallize at 23° for 6–8 hours.

11. Filter the solid, wash with 35 ml. of 1:1:2 water/methanol/IPA, and finally with 35 ml. IPA.

12. Dry in a vacuum over at 40° for 16–24 hours. Yield: 19.91–22.84 g (34–39%) IR, PMR and CMR spectral data in addition to specific rotation were completely consistent for the desired structure.

TLC System $CHCl_3$/methanol/$NH_4OH$/water (1:4:2:1) 5×20 cm. silica gel plates from Quantum Industries—1 Zone (BB-K8) having $R_f \sim 0.4$ (Ninhydrin Detection).

EXAMPLE 7

Preparation of BB-K8 by Acylation of Poly(trimethylsilyl) 6'-N-Cbz Kana A in Tetrahydrofuran With the Mixed Acid Anhydride of Pivalic Acid and BHBA A. Preparation of Mixed Anhydride BHBA (5.066 gm., 20.0 m moles), BSA (4.068 gm., 20.0 m moles) and triethylamine (2.116 g, 22.0 m moles) were dissolved in 200 ml. of sieve dried tetraydrofuran. The solution was refluxed for 2¼ hours and then chilled to −10° C. Pivaloyl chloride (2.412 gm., 20.0 m moles) was added over a period of 2–3 minutes, with stirring, and stirring was continued for 2 hours at −10° C. The temperature was then allowed to climb to 23° C.

B. Acylation of Poly(trimethylsilyl) 6'-N-Cbz Kana A

Poly(trimethylsilyl) 6'-N-Cbz Kana A prepared as in Example 1 (5.454 gm., 4.97 m moles, calculated as 6'-Cbz Kana A $(silyl)_9$) was dissolved in 50 ml. dry (molecular sieve) tetrahydrofuran at 23° C. One-half of the solution of mixed anhydride prepared in step A, above, (10.0 m moles) was added over a period of twenty minutes, with stirring, and stirring was continued for 7 days.

Water (100 ml.) was then added to the reaction mixture, and the pH (5.4) was adjusted to 2.0 with 3 M $H_2SO_4$. Stirring was continued for 1 hour and the solution was extracted with ethyl acetate. Polyacylated material began to crystallize, so the reaction mixture was filtered. After drying over $P_2O_5$, the recovered solids weighed 0.702 gms. The extraction of the reaction mixture was continued for a total of 4×75 ml. of ethyl acetate, after which the excess ethyl acetate was stripped from the aqueous layer. An aliquot of the aqueous solution was subjected to assay by HPLC. The resulting curve indicated a 26.4% yield of di-Cbz BB-K8.

The aqueous layer was then hydrogenated in a Parr apparatus at 50 p.s.i. $H_2$ pressure for two hours, using 0.5 gm. 10% Pd on carbon catalyst. The material was filtered, and the combined filtrate and washings were determined against *E. coli* to contain a 31.2% yield of BB-K8. BB-K8/BB-K29 ratio approximately 9–10/1; traces of polyacyl and unreacted Kana A present.

EXAMPLE 8

Effect of Water on the Preparation of BB-K8 by the Acylation of Poly(trimethylsilyl) Kana A in Acetone Solution at 23° C.

A. Anhydrous Solvent

Poly(trimethylsilyl) Kana A prepared as in Example 3 (2.40 gm., 2.0 m moles, calculated as Kana A $(silyl)_{10}$) was dissolved in 20 ml. of acetone which had been dried with a molecular sieve. The solution was stirred at 23° C. and a solution of SAE (0.701 gm., 2.0 m moles) in 10 ml. of sieve dried acetone was added over a period of 10 seconds. Stirring was continued at 23° C. for 22 hours. Water (50 ml.) was added and the pH (7.5) was adjusted to 2.5. The acetone was stripped in vacuo at 40° C. and the aqueous solution was then reduced at 51 p.s.i. $H_2$ pressure at 23° C. for two hours, utilizing 1.0 gm of 10% Pd on carbon as catalyst. Microbiological assay showed a 31.24% yield of BB-K8.

B. Water Added to Solvent

Step A, above, was repeated, except that 1.0 ml. (56 m moles) of water was added to the poly(trimethylsilyl) Kana A solution, and stirred for 15 minutes, prior to acylation with SAE. Microbiological assay showed a 33.80% yield of BB-K8.

EXAMPLE 9

Preparation of BB-K8 by Acylation of Poly(trimethylsilyl) 6'-N-Cbz Kana A in Acetone with the Mixed Anhydride of BHBA and Isobutylcarbonic Acid A. Preparation of Mixed Anhydride BHBA (1,267 gm., 5.0 m moles) and N-trimethylsilylacetamide (MSA) (1.313 gm., 10.0 m moles) in 20 ml. of sieve dried acetone was stirred at 23° C., and triethylamine (TEA) (0.70 ml., 5.0 m moles) were added. The mixture was refluxed under a $N_2$ atmosphere for 2½ hours. The mixture was cooled to −20° C. and isobutylchloroformate (0.751 gm., 0–713 ml., 5.50 m moles) was added. Triethylamine hydrochloride immediately began to separate. The mixture was stirred for 1 hour at −20° C.

B. Acylation

Poly(trimethylsilyl) 6'-N-Cbz Kana A prepared as in Example 1 (6.215 gm., 4.9 m moles, calculated as the $(silyl)_9$ compound) was dissolved in 20 ml. of sieve dried acetone, with stirring, at 23° C. The solution was cooled to −20° C. and the cold mixed anhydride solution from step A was slowly added over a period of 30 minutes. The reaction mixture was stirred for an additional 1½ hours at −20° C. and then for 17 hours at 23° C. The reaction mixture was then poured into 150 ml. of water at 23° C. with stirring, the pH (7.75) was adjusted to 2.5 with 3 N HCl, and stirring was continued for 15 minutes. Acetone was then stripped in vacuo at 40° C. An aliquot of the resulting aqueous solution was subjected to assay by HPLC. The resulting curve indicated a 34.33% yield of di-Cbz BB-K8.

The main portion of the aqueous solution was reduced at 50 p.s.i. $H_2$ pressure at 23° C. for 3¼ hours, utilizing 2.0 gms of Pd/C catalyst. The catalyst was removed by filtration and the combined filtrate and washings were determined by microbiological assay against *E. coli* to contain a 35.0% yield of BB-K8.

EXAMPLE 10

Preparation of BB-K8 by Acylation of Poly(trimethylsilyl) 6'-N-Cbz Kana A in 3-Pentanone Poly(trimethylsilyl) 6'-N-Cbz Kana prepared as in Example 1 (30 gm., 23.65 m moles, calculated as 6'-N-Cbz Kana A silyl)$_9$) dissolved in 100 ml. sieve dried 3-pentanone was stirred at 23° C., and NAE (26.02 m moles, 10% excess) was added over a period of 40 minutes. Stirring was continued for 113 hours at 23° C. and the mixture was then added to 250 ml. water with vigorous stirring. The pH (7.3) was adjusted to 2.5 with 3 N HCl, the mixture was stirred for an additional 30 minutes, and the 3-pentanone was stripped in vacuo at 40° C. The aqueous solution was extracted with 4×100 ml. of ethyl acetate. An aliquot of the aqueous solution was then subjected to assay by HPLC. The resulting curve indicated a 46.12% yield of di-Cbz BB-K8.

The main portion of the aqueous reaction mixture was reduced at 51.0 p.s.i. $H_2$ pressure at 23° C. for 2½ hours, utilizing 3.0 gms. of 10% Pd/C catalyst. Microbiological assay of an aliquot of the combined filtrate and washings indicated a 40.24% yield of BB-K8. The main portion of the reduced aqueous reaction mixture was then concentrated in vacuo at 40° C. to approximately 100 ml. and fractionated on a CG-50 ($NH_4+$) ion exchange column (4 inches×4 feet, containing approximately 10 liters of resin). The aqueous solution was charged on the column, the column was washed with 5 liters of water, and the material was eluted with 0.5 N $NH_4OH$ (followed by 3 N $NH_4OH$ to elute polyacylated products). Polarimetry of the fractions showed the presence of a 42.7% yield of BB-K8, a 12.0% yield of unreacted kanamycin A, a 12.4% yield of polyacylated matrial and a 23.2% yield of BB-K29.

EXAMPLE 11

Preparation of BB-K8 by Acylation of Poly(trimethylsilyl) 6'-N-Cbz Kana A in Anhydrous Cyclohexanone For Varying Times A. Poly(trimethylsilyl) 6'-N-Cbz Kana A prepared as in Example 1 (2.537 gm., 2.0 m moles, calculated as 6'-N-Cbz Kana A (silyl)$_9$) in 300 ml. dry cyclohexanone was acylated for 20 hours at 23° C. with an NAE solution in dry cyclohexanone (10.8 ml. of 0.1944 m mole/ml. solution, 2.10 m mole). The reaction mixture was then added to 150 ml. of water, with stirring, and the pH (5.6) was adjusted to 2.5 with 3 N HCl. The cyclohexanone was stripped in vacuo at 40° C. and an aliquot of the remaining aqueous phase was taken for assay by HPLC. The main portion of the aqueous phase was reduced under 50 p.s.i. $H_2$ pressure for 3 hours at 23° C., using 1.0 gm of 10% Pd/C catalyst. The catalyst was removed by filtration and the combined filtrate and washings were assayed microbiologically for BB-K8.

B. Reaction A, above, was repeated, except that the acylation was continued for 115 hours instead of 20 hours.

| | Yields | | |
|---|---|---|---|
| | HPLC Assay (di-Cbz BB-K8) | Microbiological Assay (BB-K8) | |
| | | Turbidimetric | Plate |
| Reaction A | 49.18% | 42.87% | 39.16% |
| Reaction B | 56.17% | 55.39% | 38.45% |

EXAMPLE 12

Preparation of BB-K8 by Acylation of Poly(trimethylsilyl) 6'-N-Cbz Kana A in Anhydrous Tetrahydrofuran For Varying Times A. Example 11 A was repeated except that dry tetrahydrofuran was utilized as solvent instead of dry cyclohexanone.

B. Example 11 B was repeated except that dry tetrahydrofuran was utilized as solvent instead of dry cyclohexanone.

| | Yields | | |
|---|---|---|---|
| | HPLC Assay (di-Cbz BB-K8) | Microbiological Assay (BB-K8) | |
| | | Turbidimetric | Plate |
| Reaction A | 29.27% | 28.34% | 28.18% |
| Reaction B | 33.39% | 21.52% | 28.63% |

EXAMPLE 13

Preparation of BB-K8 by Acylation of Poly(trimethylsilyl) 6'-N-Cbz Kana A in Anhydrous Dioxane For Varying Times A. Example 11 A was repeated except that the acylation was continued for 44 hours utilizing dry dioxane as the solvent.

B. Example 11 B was repeated except that the acylation was continued for 18½ hours utilizing dry dioxane as the solvent.

| | Yields | | |
|---|---|---|---|
| | HPLC Assay (di-Cbz BB-K8) | Microbiological Assay (BB-K8) | |
| | | Turbidimetric | Plate |
| Reaction A | 39.18% | 43.27% | 33.36% |
| Reaction B | 42.82% | 22.55% | 33.37% |

EXAMPLE 14

Preparation of BB-K8 by Acylation of Poly(trimethylsilyl) 6'-N-Cbz Kana A in Anhydrous Diethyl ketone at 75° C.

To a stirred solution of poly(trimethylsilyl) 6'-N-Cbz Kana A prepared as in Example 1 (2.537 gm., 2.0 m moles, calculated as 6'-N-Cbz Kana A (silyl)$_9$) in 32 ml. sieve dried diethyl ketone at 75° C. was added a solution of NAE (10.8 ml. of 0.1944 m moles/ml. of diethyl ketone, 2.10 m moles) over a period of 15 minutes. Stirring was continued at 75° C. for an additional 3 hours after which the mixture was poured into 150 ml. of water. The pH was adjusted to 2.8 with 3 N HCl and the diethyl ketone was stripped in vacuo at 40° C. HPLC assay of an aliquot of the aqueous phase indicated a 39.18% yield of di-Cbz BB-K8.

The main portion of the aqueous phase was reduced under 49.8 p.s.i. $H_2$ pressure for 3¼ hours at 23° C., using 1.0 gm of Pd/C catalyst. The catalyst was removed by filtration and the combined filtrate and washings were assayed microbiologically for BB-K8. Turbidimetric assay showed 27.84% yield and Plate assay showed 28.6% yield.

EXAMPLE 15

Preparation of BB-K8 by the Acylation of Poly(trimethylsilyl) Kana A With NAE at 0°–5° After Back Hydrolysis With Water

A. Silylation of Kanamycin A Using HMDS With TMCS as Catalyst

Kanamycin A (10 gm of 97.6% purity, 20.14 m moles) in 100 ml of sieve-dried acetonitrile was brought to reflux under a nitrogen atmosphere. A mixture of HMDS (22.76 gm, 141 m moles, 7 moles per mole of kanamycin A) and TMCS (1 ml, 0.856 gm, 7.88 m moles) was added to the refluxing reaction mixture over a period of 10 minutes. Reflux was continued for $4\frac{3}{4}$ hours and the mixture was then cooled, concentrated in vacuo to a yellow viscous syrup and dried under high vacuum for 2 hours. The yield of product was 23.8 gms (97.9%, calculated as kanamycin A (silyl)$_{10}$).

B. Acylation

Poly(trimethylsilyl) kanamycin A (23.8 gms, 20.14 m moles) prepared in step A above was dissolved in 250 ml of sieve-dried acetone at 23° and then cooled to 0°–5°. Water (3.63 ml, 201.4 m moles, 10 moles per mole of polysilylated kanamycin A) was added, with stirring, and the mixture was allowed to stand under moderate vacuum for 30 minutes, NAE (19.133 m moles, 0.95 moles per mole of polysilylated kanamycin A) in 108.3 ml of acetone was then added over a period of <1 minute. The mixture was stirred at 0°–5° for 1 hour, diluted with water, the pH adjusted to 2.5, and the acetone was then removed in vacuo. The aqueous solution was then reduced at 50 p.s.i. H$_2$ pressure at 23° for $2\frac{1}{2}$ hours using 2.0 gms of 10% Pd on carbon as a catalyst. The reduced reaction mixture was filtered through Dicalite, concentrated to ca. 100 ml in vacuo at 40° and then charged on CG-50(NH$_4$+) column (6 liters resin, 5×100 cm). It was washed with water and then eluted with 0.6 N-1.0 N-3 N NH$_4$OH. There was obtained 60.25% BB-K8, 4.37% BB-K6, 4.35% BB-K29, 26.47% kanamycin A and 2.18% polyacyls.

EXAMPLE 16

Preparation of BB-K8 by the Acylation of Poly(trimethylsilyl) 6'-N-Cbz Kana A with SAE at 0°–5° After Back Methanolysis

A. Silylation of 6'-N-Cbz Kanamycin A

6'-N-Cbz kanamycin A (20.0 gm, 32.4 m moles) in 200 ml of sieve-dried acetonitrile was brought to reflux under a nitrogen atmosphere. HMDS (47.3 ml, 226.8 m moles, 7 moles per mole of 6'-N-Cbz kana A) was added over a 10 minute period and reflux was continued for 20 hours. The mixture was then cooled, concentrated in vacuo, and dried under high vacuum for 2 hours to give 39.1 gms of white amorphous solid (95.4% yield, calculated as 6'-N-Cbz kana A (silyl)$_9$).

B. Acylation

Poly(trimethylsilyl) 6'-N-Cbz kana A (39.1 gm, 32.4 m moles) prepared in step A above was dissolved in 400 ml of dry acetone, with stirring, at 23°. Methanol (6.6 ml, 162 m moles, 5 moles per mole of polysilylated 6'-N-Cbz kana A) was added and the mixture was stirred at 23° for 1 hour under a strong nitrogen purge. The mixture was cooled to 0°–5° and a solution of SAE (11.35 gm, 32.4 m moles) in 120 ml of pre-cooled, dry acetone was added. The mixture was stirred for an additional 3 hours at 0°–5° and then placed in a 4° cold room for 1 week. Water (300 ml) was added, the pH was adjusted to 2.0, the mixture was stirred for 1 hour, and the acetone was then stripped in vacuo. The resultant aqueous solution was reduced at 54.0 p.s.i. H$_2$ pressure for 17 hours at 23° utilizing 3.0 gm of 10% Pd on carbon as catalyst. It was then filtered through Dicalite, concentrated in vacuo to 75-100 ml, charge on a CG-50(NH$_4$+) column and eluted with water and 0.6 N NH$_4$OH. There was obtained 52.52% BB-K8, 14.5% BB-K29, 19.6% kanamycin A and 1.71% polyacyls.

EXAMPLE 17

Preparation of BB-K8 by the Acylation of Poly(trimethylsilyl) Kana A With SAE at 0°–5° After Back Hydrolysis With Water

A. Silylation of Kanamycin A With TMCS in Acetonitrile Using Tetramethylguanidine as Acid Acceptor Kanamycin A (4.88 gm, 10.07 m mole) was suspended in 100 ml of sieve-dried acetonitrile with stirring at 23°. To the stirred suspension was added tetramethylguanidine (TMG) (16.234 gm, 140.98 m moles, 14 moles per mole of kanamycin A). The mixture was heated to reflux and TMCS (15.32 gm, 140.98 m moles, 14 moles per mole of kanamycin A) was added over a 15 minute period. A white precipitate of TMG.HCl formed after about one-half of the TMCS had been added. The mixture was cooled to room temperature, concentrated to a tacky residue and dried under high vacuum for 2 hours. The solid was triturated with dry THF (100 ml), and the insoluble TMG.HCl was filtered off and washed with 5×20 ml portions of THF. The combined filtrate and washings were concentrated in vacuo at 40° to a tacky residue and dried under high vacuum for 2 hours. There was obtained 10.64 gms of a light cream tacky residue (87.6% yield, calculated as kanamycin A (silyl)$_{10}$).

B. Acylation

Poly(trimethylsilyl) kanamycin A (10.64 gm, 10.07 m moles) prepared in step A above was dissolved in 110 ml of sieve-dried acetone, with stirring, at 23° and the solution was cooled to 0°–5°. Water (1.81 ml, 100.7 m moles, 10 moles per mole of polysilylated kana A) was added and the solution was stirred for 30 minutes under moderate vacuum. SAE (3.70 gm, 10.57 m moles, 5% excess) in 40 ml of pre-cooled dry acetone was added over a period of <1 minute, and the mixture was stirred for one hour. The mixture was worked up by the general procedure in Example 16B to give ca. 50% BB-K8, ca. 10% BB-K29, 5-8% BB-K6, ca. 20% kanamycin A and 5-8% polyacyls.

EXAMPLE 18

Preparation of Poly(trimethylsilyl) Kanamycin A in Pyridine Using HMDS

Kanamycin A (10.0 gms, 20.64 m moles) was suspended in 100 ml sieve-dried freshly distilled pyridine at 23°. A nitrogen purge was started and the suspension was brought to reflux. HMDS (17.33 gms, 107.32 m moles, 5.2 moles per mole of kanamycin A) was added over a period of 10 minutes and the mixture was refluxed for 19 hours. It was then cooled to room temperature, concentrated in vacuo to a light yellow-gold syrup, and dried under high vacuum to a white amorphous solid. There was obtained 22.1 gms (92.6% yield, calculated as kanamycin A (silyl)$_{10}$).

EXAMPLE 19

Preparation of Poly(triethylsilyl) Kanamycin A Using Triethylchlorosilane With Triethylamine as Acid Acceptor Kanamycin A (5.0 gms of 97.6% purity, 10.07 m moles) was suspended in 100 ml of sieve-dried acetonitrile at 23°. Triethylamine (TEA) (33.8 ml, 24.5 gm, 241.7 m moles) was added and the suspension was brought to reflux. A solution of trichloroethylsilane (23.7 ml, 21.3 gm, 140.98 m moles) in 25 ml dry acetonitrile was added over a 20 minute period. Reflux was continued for an additional 7 hours and the mixture was cooled to room temperature, whereupon long fine needles of TEA.HCl separated out. The mixture was allowed to stand at room temperature for ca. 16 hours, concentrated in vacuo at 40° to a tacky solid and dried for 2 hours under high vacuum to a deep orange tacky solid. The solid was triturated with 100 ml dry THF at 23° and the insoluble TEA.HCl was filtered off, washed with 5×20 ml of THF, and dried to give 16.0 gms of TEA.HCl. The combined filtrate and washings were concentrated in vacuo to a solid and dried under high vacuum for 2 hours. There was obtained 19.3 gms of poly(triethylsilyl) kanamycin A as a deep orange viscous syrup.

EXAMPLE 20

Preparation of Poly(trimethylsilyl) Kanamycin A Using bis-Trimethylsilylurea Kanamycin A (10.0 gm of 99.7% purity, 20.58 m moles) was suspended in 200 ml of sieve-dried acetonitrile, with stirring, at 23°. To the suspension was added bis-trimethylsilylurea (BSU) (29.45 gms, 144.01 m moles, 7 moles per mole of kanamycin), and the mixture was brought to reflux under a nitrogen atmosphere. Reflux was continued for 17 hours and the reaction mixture was then cooled to room temperature. A small amount of insoluble material present was removed by filtration, washed with 3×10 ml portions of acetonitrile and dried (1.1381 gms). Infrared showed this to be BSU plus a small amount of unreacted kanamycin A. The combined filtrate and washings were cooled at 4° for 16 hours. Additional solid separated, was recovered as above, (7.8 gms) and was shown by infrared to be BSU plus urea. The light yellow filtrate and washings were concentrated in vacuo at 40° and dried under high vacuum to give 27.0 gm of a white solid which was partly tacky and partially fine needle-like crystals. The solid was treated with 150 ml of heptane at 23°, the insoluble portion was removed by filtration, washed with 2×50 ml portions of heptane and dried, to give 6.0 gms of white needles (shown by infrared to be BSU plus urea). The combined filtrate and washings were concentrated in vacuo at 40° and dried under high vacuum for 2 hours to give 20.4 gms of white needles, the infrared spectrum of which was typical for polysilylated kanamycin A. Calculations showed the product to contain an average of 7.22 trimethylsilyl groups.

EXAMPLE 21

Preparation of BB-K8 by the Acylation of Per(trimethylsilyl) Kanamycin A After Partial Desilylation With 1,3-Butanediol A. Preparation of Per(trimethylsilyl) kanamycin A Kanamycin A (10.0 gm, 20.639 m moles) was suspended in 100 ml of sieve-dried acetonitrile, with stirring, at 23°. The suspension was brought to reflux under a nitrogen purge and HMDS (23.322 gms, 144.5 m moles, 7 moles per mole of kanamycin A) was added over a period of ten minutes. Reflux was continued for 16 hours and the mixture was then cooled to room temperature, concentrated in vacuo and dried for 2 hours under high vacuum. There was obtained 24.3 gm of a white, tacky residue (92.1% yield, calculated as kanamycin A (silyl)$_{11}$).

B. Acylation

Per(trimethylsilyl) kanamycin A (24.3 gm) prepared in step A above was dissolved in 240 ml of sieve-dried acetone, with stirring, at 23°. To this solution was added 1,3-butanediol (9.25 ml, 103.2 m mole, 5 moles per mole of per(trimethylsilyl) kanamycin A. The mixture was stirred at 23° for 2 hours under a nitrogen purge and then cooled at 0°–5°. SAE (7.23 gm, 20.64 m moles) in 70 ml of pre-cooled acetone was added over a period of about 1 minute. The mixture was stirred at 0°–5° for 3 hours and then allowed to stand in a 4° cold room for ca. 16 hours. Water (200 ml) was added, the pH was adjusted to 2.5 and the clear yellow solution was stirred at 23° for 30 minutes. The acetone was stripped in vacuo and the aqueous solution was reduced at 55.0 p.s.i. H$_2$ pressure at 23° for 2 hours using 3.0 gm of 10% Pd on carbon as catalyst. The reduced solution was filtered through Dicalite and chromatographed as in Example 16B to give 47.50% BB-K8, 5.87% BB-K29, 7.32% BB-K6, 24.26% kanamycin A and 7.41% polyacyls.

EXAMPLE 22

Preparation of BB-K8 by the Acylation of Poly(trimethylsilyl) Kanamycin A Prepared in THF Using SAE With Sulfamic Acid Catalyst To a refluxing mixture of kanamycin A (5.0 gm, 10.32 m moles) in 50 ml of sieve-dried tetrahydrofuran (THF) were added sulfamic acid (100 mg) and HMDS (12.32 gm, 76.33 m moles). The mixture was refluxed for 18 hours, with complete solution occurring after 6 hours. The solution was cooled to 23°, treated with 0.1 ml of water and held at 23° for 30 minutes. After stirring for 3 hours, the mixture was diluted with 100 ml of water and the pH was adjusted to 2.2 with 10% H$_2$SO$_4$. It was stirred for 30 minutes at 23° and then concentrated in vacuo to remove THF. The resulting aqueous solution was reduced at 50 p.s.i. H$_2$ pressure for 2 hours at 23° using 10% Pd on carbon as a catalyst. The reduced solution was filtered through Dicalite and the solids were washed with water. The combined filtrate and washings (150 ml) were determined by microbiological assay against *E. coli* to contain 1225 mcg/ml (31.5% activity yield) of BB-K8.

EXAMPLE 23

Preparation of BB-K8 by the Acylation of Poly(trimethylsilyl) Kanamycin A with the N-Hydroxysuccinimide Ester of Di-Carbobenzyloxy AHBA

A. Preparation of Dicarbobenzyloxy L-(−)-α-Amino-α-hydroxybutyric Acid N-Hydroxysuccinimide Ester Dicarbobenzyloxy L-(−)-α-amino-α-hydroxybutyric acid (8 gm, 20.65 m moles) and N-hydroxysuccinimide (2.37 gm, 20.65 m moles) were dissolved in 50 ml of dry acetone at 23°. Dicyclohexylcarbodiimide (4.25 gm, 20.65 m moles) dissolved in 20 ml of dry acetone was added and the total was agitated at 23° for 2 hours. Dicyclohexylurea was filtered off, the filter cake was washed with 10 ml of dry acetone, and the filtrate and washings were combined.

B. Acylation

Poly(trimethylsilyl) kanamycin A, prepared according to the general procedure of Example 21 from 10.0 gms (20.639 m moles) of kanamycin A, was dissolved in 100 ml of dry acetone. The solution was cooled to 0°–5°, 3.7 ml of deionized water was added, and the solution was stirred at 0°–5° for 30 minutes under moderate vacuum.

To this solution was added the solution of the di-Cbz-blocked acylating agent prepared in step A, and the mixture was stirred at 0°14 5° for 30 minutes. The mixture was diluted with water, the pH was adjusted to 2.2 and the acetone was removed in vacuo. The aqueous solution was reduced by the general procedure of Example 22 and then filtered through Dicalite. Chromatography showed 40–45% BB-K8, ca. 10% BB-K29, a trace of BB-K6, ca. 30% kanamycin A and a small amount of polyacyls.

EXAMPLE 24

Preparation of Poly(trimethylsilyl) Kanamycin A Using HMDS with Imidazole as Catalyst Kanamycin A (11 gm, 22.7 m moles) and 100 mg of imidazole were heated to reflux in 100 ml of sieve-dried acetonitrile, under a nitrogen purge. HMDS (18.48 gm, 114.5 m moles, 5 moles per mole of kanamycin A) was added over a period of 30 minutes and the mixture was refluxed for 20 hours. Complete solution occurred in ca. 2½ hours. The solution was cooled to 23° and the solvent was removed in vacuo to leave 21.6 gms of poly(trimethylsilyl) kanamycin A as a foamy residue (93.1% yield, calculated as kanamycin(silyl)$_{11}$).

EXAMPLE 25

Preparation of 1-N-[L-(−)-γ-Amino-α-hydroxybutyryl]kanamycin B (BB-K26)by the Acylation of Poly(trimethylsilyl) Kanamycin B With SAE

A. Preparation of Poly(trimethylsilyl) Kanamycin B Using HMDS With TMCS Catalyst Kanamycin B (25 gm, 51.7 m moles) in 250 ml of sieve-dried acetonitrile was heated to reflux under a stream of nitrogen. HMDS (62.3 gm, 385.81 m moles, 7.5 moles per mole of kanamycin B) was added over a period of 30 minutes followed by 1 ml of TMCS as catalyst. The mixture was refluxed for 21 hours with complete solution after 1 hour. The solvent was then removed in vacuo at 60° and the oily residue was held at 60° under high vacuum for 3 hours. There was obtained 53.0 gm of poly(trimethylsilyl) kanamycin B (85.2% yield, calculated as kanamycin B (silyl)$_{10}$).

B. Acylation

The poly(trimethylsilyl) kanamycin B prepared in step A above (53.0 gm ) was dissolved in 500 ml of dry acetone at 0°–5°, methanol (20.9 ml) was added, and the mixture was stirred in vacuo for 30 minutes at 0°–5°. A solution of SAE (18.1 gm, 51.67 m moles) in 200 ml of pre-cooled dry acetone was added over a period of less than 1 minute and the mixture was stirred for 30 minutes at 0°–5°. The mixture was worked up according to the general procedure of Example 22 and then loaded on a column of CG-50 (NH$_4$+) (8×120 cm). It was eluted with an NH$_4$OH gradient from 0.6 N to 3 N. There was obtained 38% of BB-K26, 5% of the corresponding 6'-N-acylated kanamycin B (BB-K22), 10% of the corresponding 3-N-acylated kanamycin B (BB-K46) 14.63% kanamycin B and a small amount of polyacylated kanamycin B.

EXAMPLE 26

Preparation of Poly(trimethylsilyl) Kanamycin A Using HMDS With Kanamycin A Sulfate as Catalyst Kanamycin A (19.5 gm, 40.246 m moles) and kanamycin A sulfate (0.5 gm, 0.858 m mole) [total=20.0 gm, 41.0 m moles] in 200 ml of sieve-dried acetonitrile was brought to reflux. HMDS (60.3 ml, 287.7 m moles, 7 moles per mole of kanamycin A) was slowly added and the mixture was refluxed for 28 hours. It was then stripped to dryness on a rotary evaporator and dried under steam injector vacuum. There was obtained 47.5 gms of poly(trimethylsilyl) kanamycin A as a pale yellow oil (95.82% yield, calculated as kanamycin A (silyl)$_{10}$).

EXAMPLE 27

Preparation of BB-K8 by the Acylation of Poly(trimethylsilyl) Kanamycin A With N-Trifluoroacetyl Blocked AHBA N-Hydroxysuccinimide Ester

A. Preparation of N-Trifluoroacetyl AHBA and Conversion to its N-Hydroxysuccinimide Ester To a suspension of AHBA (5.0 gm, 42 m moles) in 100 ml THF was added trifluoroacetic anhydride (40 gm, 191 m moles), with stirring, over a 10 minute period. The solution was stirred for 18 hours at 23° and then concentrated to dryness in vacuo at 50°. The residue was dissolved in 100 ml of aqueous methanol (1:1) and stirred for 1 hour. It was then concentrated to dryness in vacuo and redissolved in 50 ml H$_2$O. The aqueous solution was extracted with 3×50 ml portions of MIBK and, after drying over Na$_2$SO$_4$, the extract was concentrated to an oil. Traces of solvent were removed by adding and distilling off 4 ml of water. On standing the oil changed to a waxy, crystalline solid (2.5 gm, 28% yield.

The N-trifluoroacetyl AHBA (2.4 gm, 11.3 m moles) was dissolved in 50 ml dry acetone and N-hydroxysuccinimide (1.30 gm, 11.31 m moles) was added to the solution. A solution of dicyclohexylcarbodiimide (2.33 gm) in 20 ml of dry acetone was slowly added. The reaction mixture was stirred for 2 hours at 23° and the precipitated dicyclohexylurea was removed by filtration and washed with a small amount of acetone. The combined filtrate and washings (a solution of the N-hydroxysuccinimide ester of N-trifluoroacetyl AHBA) was utilized in the next step without isolation.

B. Acylation

To a solution of poly(trimethylsilyl) kanamycin A prepared as in Example 26 (11.31 m moles) in 54 ml of acetone was added 2.0 ml (113.4 m moles) of water, and the mixture was stirred in vacuo at 0°-5° for 30 minutes. The N-hydroxysuccinimide ester of N-trifluoroacetyl AHBA prepared in step A above (11.31 m moles) was added to the mixture and it was then held at 5° for 1 hour. The pH was then adjusted to ca. 2.0 with 20% $H_2SO_4$, the mixture was stirred for 30 minutes and the pH was then raised to ca. 6.0 with $NH_4OH$. The mixture was then stripped to dryness in a rotary evaporator to give 14.4 gm of a tacky off-white solid. The solid was dissolved in 100 ml of water, the pH was raised from 5.5 to 11.0 with 10 N $NH_4OH$ and the solution was heated in an oil bath at 70° for 1 hour. The pH (9.5) was then lowered to 7.0 with HCl, the solution was polish filtered to remove a small amount of insolubles and the filter was washed with water. The combined filtrate and washings (188 ml) was applied to a CG-50 ($NH_4^+$) column (8×90 cm), washed with 2 liters of water and eluted with a $NH_4OH$ gradient (0.6 N-1.0 N-concentrated). There was obtained 28.9% BB-K8, 5.0% BB-K6, 5.7% BB-K29, 43.8% kanamycin A, 3.25% polyacyls plus 14.3% of an unknown material which was in the first fraction off the column.

EXAMPLE 28

Preparation of BB-K8 by the Acylation of Poly(trimethylsilyl) Kanamycin A With t-Butyloxycarbonyl Blocked AHBA N-Hydroxysuccinimide Ester.

A. Preparation of t-BOC AHBA and Conversion to its N-Hydroxysuccinimide Ester

A solution of AHBA (5.0 gm, 42 m moles) in 100 ml of water and 20 ml of acetone was adjusted to pH 10 with 10 N NaOH. Over a period of 3-4 minutes was added 11.6 gm (53 m moles) of di-t-butyl dicarbonate, and the solution was stirred for 35 minutes while maintaining the pH at 10 by the periodic addition of 10 N NaOH. The acetone was removed in vacuo and the aqueous phase was washed with 40 ml of ethyl acetate. The pH of the aqueous solution was lowered to 2.0 with 3 N HCl and it was then extracted with 3×30 ml of MIBK. The combined MIBK extracts were dried over $Na_2SO_4$ and concentrated to a clear oily residue (8.2 gm, 89%).

The t-BOC-AHBA (4.25 gm, 19.4 m moles) was dissolved in 50 ml of acetone and N-hydroxysuccinimide (2.23 gm, 19.4 m moles) was added. A solution of dicyclohexylcarbodiimide (4.00 gm 19.4 m moles) in 20 ml of acetone was slowly added and the mixture was stirred for 2 hours at 23°. The precipitated dicyclohexylurea was removed by filtration and was washed with a small amount of acetone. The combined filtrate and washings (a solution of the N-hydroxysuccinimide ester of t-BOC-AHBA) was utilized in the next step without isolation.

B. Acylation

To a solution of poly(trimethylsilyl) kanamycin A prepared as in Example 26 (41.28 m moles) in 94 ml of acetone was added 3.5 ml (194 m moles) of water, and the mixture was stirred in vacuo at 0°-5° for 30 minutes. The N-hydroxysuccinimide ester of t-BOC-AHBA prepared in step A above (19.4 m moles) was added and the mixture was allowed to stand at 5° for 1 hour. Water (200 ml) was added and the pH (7.0) was lowered to 2.0 with 20% $H_2SO_4$. After 30 minutes stirring the pH was raised to ca. 6.0 with $NH_4OH$ and the mixture was stripped to dryness in vacuo to give 36.3 gms of a golden oil. The oil was dissolved in 200 ml of trifluoroacetic acid, allowed to stand for 15 minutes and stripped to dryness in a rotary evaporator. The oil was washed with water and the water was flashed off. Concentrated $NH_4OH$ was added to pH 6.0 and was flashed off. The resulting solid was dissolved in water, filtered, and the filter washed with water. The combined filtrate and washings (259 ml) were loaded on a CG-50 ($NH_4^+$) column (8×92 cm), washed with 4 liters of water and eluted with an $NH_4OH$ gradient (0.6 N-1.0 N-concentrated). There was obtained 40.32% BB-K8, 4.58% BB-K6, 8.32% BB-K29, 30.50% kanamycin A and 7.43% polyacyls.

EXAMPLE 29

The general procedure of Example 1 is repeated, except that the 6'-N-carbobenzyloxykanamycin A used therein is replaced by an equimolar weight of 6'-N-carbobenzyloxykanamycin B, and there is thereby produced 1-N-[L-(−)-γ-amino-α-hydroxybutyryl]kanamycin B.

EXAMPLE 30

The general procedure of Example 1 is repeated except that the L-(−)-γ-benzyloxycarbonylamino-α-hydroxybutyric acid N-hydroxy-5-norbornene-2,3-dicarboximide ester used therein is replaced by
L-(−)-β-benzyloxycarbonylamino-α-hydroxypropionic acid N-hydroxy-5-norbornene-2,3-dicarboximide ester and
L-(−)-δ-benzyloxycarbonylamino-α-hydroxyvaleric acid N-hydroxy-5-norbornene-2,3-dicarboximide ester, respectively,
and there is thereby produced
1-N-[L-(−)-β-amino-α-hydroxypropionyl]kanamycin A and
1-N-[L-(−)-δ-amino-α-hydroxyvaleryl]kanamycin A, respectively.

EXAMPLE 31

The general procedure of Example 25 is repeated except that the L-(−)-γ-benzyloxycarbonylamino-α-hydroxybutyric acid N-hydroxyester used therein is replaced by
L-(−)-β-benzyloxycarbonylamino-α-hydroxy propionic acid N-hydroxysuccinimide ester and
L-(−)-δ-benzyloxycarbonylamino-α-hydroxyvaleric acid N-hydroxysuccinimide ester, respectively,
and there is thereby produced
1-N-[L-(−)-β-amino-α-hydroxypropionyl]kanamycin B and
1-N-[L-(−)-δ-amino-α-hydroxyvaleryl]kanamycin B, respectively.

EXAMPLE 32

Preparation of BB-K8 by the Acylation of Poly(trimethylsilyl) 3,6′-Di-N-Carbobenzyloxykanamycin A in Anhydrous Diethyl Ketone

A. 3,6′-Di-N-carbobenzyloxykanamycin A

A suspension of 7.26 g (15 m moles) of kanamycin A (free base) and 18.6 g (75 m moles) of nickel acetate tetrahydrate in 300 ml of dimethylsulfoxide (DMOS) was heated at 100° C. for about 30 minutes, with stirring, until a clear, green solution was obtained. After cooling, a solution of 11.8 g (37.6 m moles) of N-carbobenzyloxy-5-norbornene-2,3-dicarboximide in 50 ml of DMSO was added to the solution. The mixture was stirred at room temperature overnight, treated with 100 ml of concentrated ammonia water and 1 liter of water, stirred at room temperature for 1 hour, and applied to the top of a Diaion HP-10 column (300 ml). The column was subjected to stepwise elution beginning with 7 N NH$_4$OH, then with methanol-water (1:1) and finally with methanol-water (10:1), collecting 20 ml fractions and monitoring by thin layer chromatography on Merck Silica Gel 60 F-254 plates using chloroform-ethanol-28% ammonium hydroxide (1:2:1). A portion of the desired product which crystallized as fine needles from fractions containing the product at high concentrations was filtered off to provide an analytical sample. The filtrate and other fractions containing the desired product (RF 0.42) were combined, and the solution was evaporated in vacuo. The residue was triturated with diethyl ether to give a total of 9.7 g (86%) of the title product. Mp >300° C. IR(KBr): $\nu_{c=o}$ 1690 cm$^{-1}$. NMR(DMSO-d$_6$+DCl, pD ca 3): δ4.76-5.26 (6H,m,H$_1$′,H$_1$″) and CO-OCH$_2$-C$_6$H$_5$×2), 7.26(10H,s,CO-OCH$_2$-C$_6$H$_5$×2).

Anal. Calcd. for C$_{34}$H$_{48}$N$_4$O$_{15}$·H$_2$O: C, 52.98; H, 6.54; N, 7.27. Found: C, 53.20; H, 6.42; N, 7.04.

B. Poly(trimethylsilyl) 3,6′-Di-N-carbobenzyloxykanamycin A

A mixture of 1.5 g (2 m moles) of 3,6′-di-N-carbobenzyloxykanamycin A from Step A, above, and 1.29 g (8 m moles) of hexamethyldisilazane in 15 ml of dry acetonitrile was refluxed for 16 hours. The clear solution was concentrated to dryness in vacuo and the residue was dissolved in 20 ml of dry diethyl ketone. The solution was used directly in the next step.

C. Acylation of Poly(trimethylsilyl) 3,6′-Di-N-carbobenzyloxykanamycin A Utilizing an Equimolar Amount of Acylating Agent To the solution from Step B, above, was added, with stirring, 700 mg (2 m moles) of L-(−)-α-carbobenzyloxyamino-α-hydroxybutyric acid N-hydroxysuccinimide ester (SAE). The mixture was stirred at room temperature for 19 hours, then treated with 8 ml of water and 35 ml of tetrahydrofuran (THF), adjusted to pH 3 with aqueous hydrochloric acid, stirred for 30 minutes and concentrated to dryness in vacuo. The residue was dissolved in a mixture of 30 ml of water, 40 ml of methanol, 10 ml of n-butanol and 40 ml of THF, and hydrogenated overnight in the presence of 500 mg of 10% palladium on carbon. The catalyst was removed by filtration and the filtrate was evaporated in vacuo and lyophilized to give 1.7 g of crude BB-K8. The amorphous powder was redissolved in water, and the solution was adjusted to pH 4 with aqueous hydrochloric acid and chromatographed on a column of Amberlite CG-50 in the NH$_4$$^+$ cycle. The column was subjected to stepwise elution with water, 0.1 N NH$_4$OH, 0.3 N NH$_4$OH, 0.5 N NH$_4$OH and 2 N NH$_4$OH, collecting 10-ml fractions and monitoring by thin layer chromatograph using Merck Silica Gel 60 F-254 plates using chloroform-methanol-28% ammonium hydroxide-water (1:4:2:1). The homogeneous fractions were combined, evaoporated and finally lyophilized. Fractions containing BB-K8 and fractions containing recovered kanamycin A were assayed using *K. pneumoniae* A20680 and *B. subtilis* PCI 129, respectively.

| Fraction Nos. | NH$_4$OH (N) | Weight | Yield (%) | Product | Rf value |
|---|---|---|---|---|---|
| 32–39 | 0.1, 0.3 | 102 mg | | partially deblocked product | |
| 40–46 | 0.3 | 174 mg$^a$ | 7$^c$ | kanamycin A | 0.42 |
| 47–59 | 0.3, 0.5 | 106 mg | | unidentified product | 0.33 |
| 60–78 | 0.5 | 816 mg$^b$ | 67$^c$ | BB-K8 | 0.18 |
| 89–95 | 2 | 70 mg | 5 | diacyl-kanamycin A | 0.05 |

$^a$408 mcg/mg.
$^b$956 mcg/mg.
$^c$based on bioassay.

Hydrogenolysis of the partially deblocked product with Pd-C followed by isolation on an CG-50 column gave an additional 30 mg (2%) of BB-K8. The total yield of BB-K8 amounted to 846 mg (69%).

D. Acylation of Poly(trimethylsilyl) 3,6′-Di-N-carbobenzyloxykanamycin A Utilizing 1.2 Equivalents of Acylating Agent Step C, above, was repeated except that 20% excess acylating agent was utilized. The following results were obtained.

| Fraction Nos. | NH$_4$OH (N) | Weight | Yield (%) | Product | Rf value |
|---|---|---|---|---|---|
| 28–29 | 0.2 | 107 mg | | partially deblocked product | |
| 30–41 | 0.2 | 157 mg | | unidentified product | 0.35 |
| 42–52 | 0.3 | 120 mg | | unidentified product | 0.30 |
| 53–81 | 0.3, 0.5 | 750 mg$^a$ | 60$^b$ | BB-K8 | 0.14 |
| 94–116 | 1, 2 | 147 mg | 11 | diacyl-kanamycin A | 0.05 |

$^a$933 mcg/mg.
$^b$based on bioassay.

Hydrogenolysis of the partially deblocked product with Pd-C followed by isolation on an CG-50 column gave an additional 21 mg (2%) of BB-K8. The total yield of BB-K8 amounted to 771 mg (62%).

E. Acylation of Poly(trimethylsilyl) 3,6′-Di-N-carbobenzyloxykanamycin A Utilizing 1.5 Equivalents of Acylating Agent Step C, above, was repeated except that 50% excess acylating agent was utilized. The following results were obtained.

| Fraction Nos. | NH₄OH (N) | Weight | Yield (%) | Product | Rf value (twice-developed) |
|---|---|---|---|---|---|
| 29–39 | 0.2 | 293 mg | | partially deblocked product | |
| 40–47 | 0.3 | 95 mg[a] | 6[c] | kanamycin A | 0.67 |
| 65–80 | 0.5 | 582 mg[b] | 29[c] | BB-K8 | 0.33 |
| 100–130 | 1, 2 | 543 mg | 26 | diacyl-kanamycin A | 0.09 |

[a]860 mcg/mg.
[b]880 mcg/mg.
[c]based on bioassay.

We claim:

1. The process for the preparation of a 1-N-[ω-amino-α-hydroxyalkanoyl]kanamycin A or B having the formula

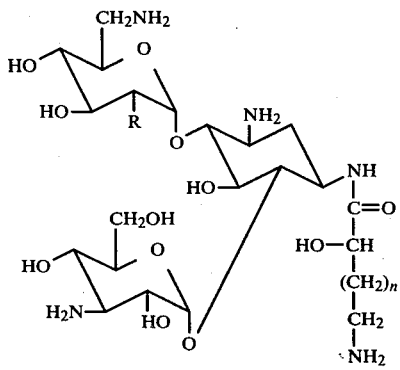

in which R is OH or NH₂ and n is an integer of from 0 to 2, or a nontoxic pharmaceutically acceptable acid addition salt thereof, which comprises acylating polysilylated kanamycin A or B or polysilylated kanamycin A or B containing a conventional non-silyl amino-blocking group on the 3-amino group, the 6'-amino group or the 3-amino and 6'-amino groups, with an acylating derivative of the acid of the formula

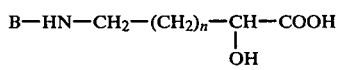

in which n is an integer of from 0 to 2 and B is a conventional amino-blocking group, in a substantially anhydrous organic solvent, and subsequently removing all blocking groups by conventional means; wherein the silyl moieties on the polysilylated kanamycin A or B are selected from trimethylsilyl, triethylsilyl, tri-n-propylsilyl, methyldichlorosilyl, dimethylchlorosilyl, methyldiethylsilyl, dimethylethylsilyl, dimethyl-t-butylsilyl, phenyldimethylsilyl, benzylmethylethylsilyl, phenylmethylethylsilyl, triphenylsilyl, tri-o-tolylsilyl, tri-p-tolylsilyl and tri-p-dimethylaminophenylsilyl, and wherein the amino-blocking groups on the starting polysilylated kanamycin A or B and on the acylating derivative of the acid are independently selected from those of the formulae

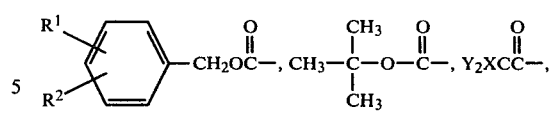

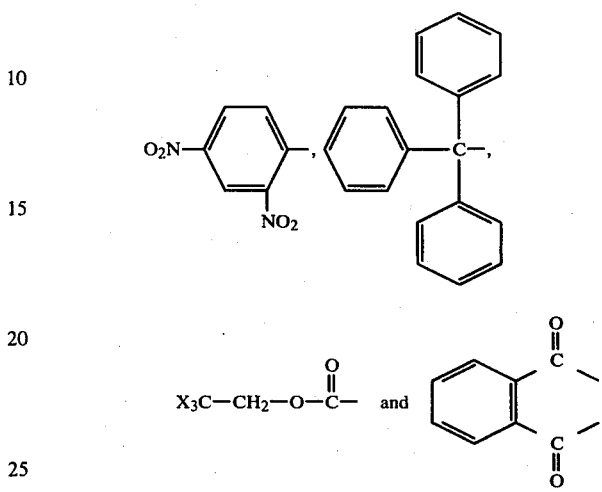

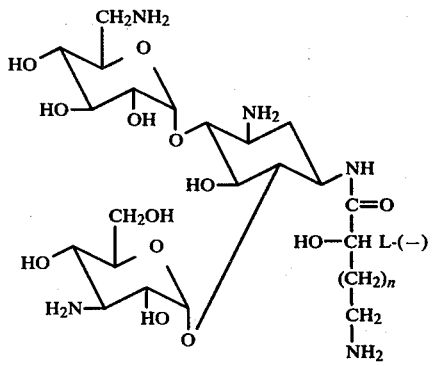

wherein R¹ and R² are alike or different and each is H, F, Cl, Br, NO₂, OH, (lower)alkyl or (lower)alkoxy, X is Cl, Br, F or I and Y is H, Cl, Br, F or I.

2. The process for the preparation of a 1-N-[L-(−)-ω-amino-α-hydroxyalkanoyl]kanamycin A having the formula

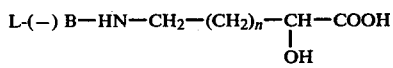

in which n is an integer of from 0 to 2, or a nontoxic pharmaceutically acceptable acid addition salt thereof, which comprises acylating polysilylated kanamycin A with an acylating derivative of the acid of the formula L-(−) B—HN—CH₂—(CH₂)ₙ—CH—COOH
                                    |
                                    OH in which n is an integer of from 0 to 2 and B is a conventional amino-blocking group, in a substantially anhydrous organic solvent, and subsequently removing all blocking groups by conventional means; wherein the silyl moieties on the polysilylated kanamycin A are selected from trimethylsilyl, triethylsilyl, tri-n-propylsilyl, methyldichlorosilyl, dimethylchlorosilyl, methyldiethylsilyl, dimethylethylsilyl, dimethyl-t-butylsilyl, phenyldimethylsilyl, benzylmethylethylsilyl, phenylmethylethylsilyl, triphenylsilyl, tri-o-tolylsilyl, tri-p- tolylsilyl and tri-p-dimethylaminophenylsilyl, and the amino-blocking group on the acylating derivative of the acid is selected from those of the formulae

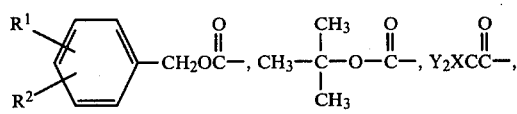

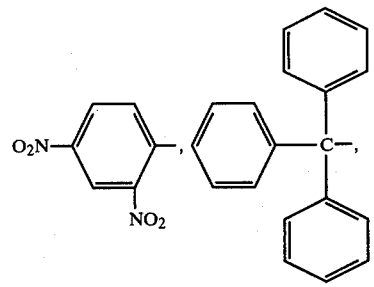

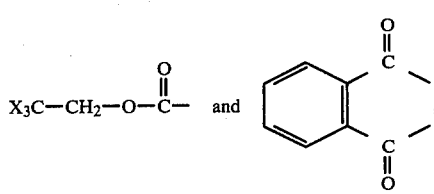

wherein $R^1$ and $R^2$ are alike or different and each is H, F, Cl, Br, $NO_2$, OH, (lower)alkyl or (lower)alkoxy, X is Cl, Br, F or I and Y is H, Cl, Br, F or I.

3. The process of claim 2 wherein the acylating derivative of the acid is an active ester or a mixed acid anhydride.

4. A process of claim 3 in which the polysilylated kanamycin A starting material contains an average number of silyl groups per molecule of from 4 to 8, n is 1 and the silyl groups are trimethylsilyl.

5. The process of claim 3 wherein the polysilylated kanamycin A contains a conventional non-silyl amino-blocking group selected from those of the formulae

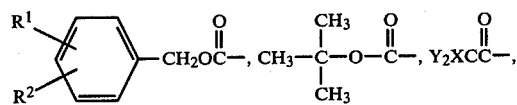

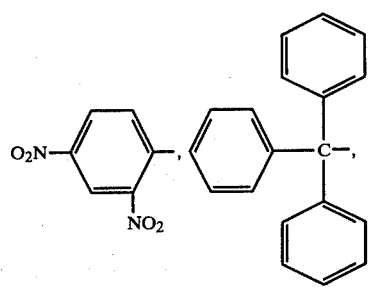

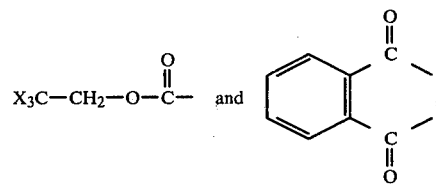

wherein $R^1$ and $R^2$ are alike or different and each is H, F, Cl, Br, $NO_2$, OH, (lower)alkyl or (lower)alkoxy, X is Cl, Br, F or I and Y is H, Cl, Br, F or I on the 6'-amino group.

6. A process of claim 5 in which the polysilylated kanamycin A starting material contains an average number of silyl groups per molecule of from 3 to 7.

7. A process of claim 6 in which the amino-blocking group on the 6'-amino group of the polysilylated kanamycin A is the carbobenzyloxy group, n is 1 and the silyl groups are trimethylsilyl.

8. The process of claim 3 wherein the polysilylated kanamycin A contains conventional non-silyl amino-blocking groups selected from those of the formulae

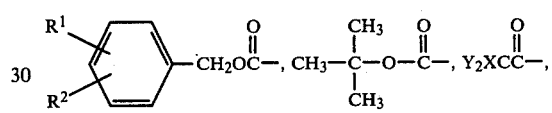

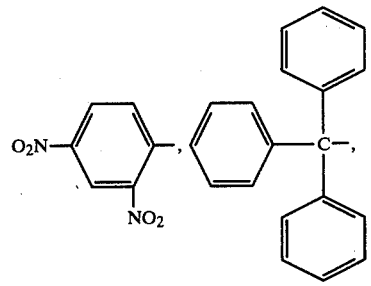

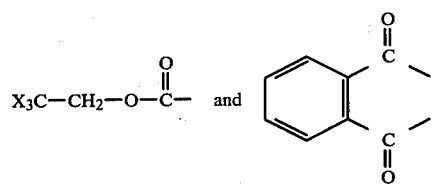

wherein $R^1$ and $R^2$ are alike or different and each is H, F, Cl, Br, $NO_2$, OH, (lower)alkyl or (lower)alkoxy, X is Cl, Br, F or I and Y is H, Cl, Br, F or I on the 3-amino and 6'-amino groups.

9. A process of claim 8 in which the polysilylated kanamycin A starting material contains an average number of silyl groups per molecule of from 3 to 6.

10. A process of claim 9 in which the amino-blocking groups on the 3-amino and 6'-amino groups of the polysilylated kanamycin A are carbobenzyloxy groups, n is 1 and the silyl groups are trimethylsilyl.

11. The process for the preparation of a 1-N-[L-(—)-ω-amino-α-hydroxyalkanoyl]kanamycin B having the formula

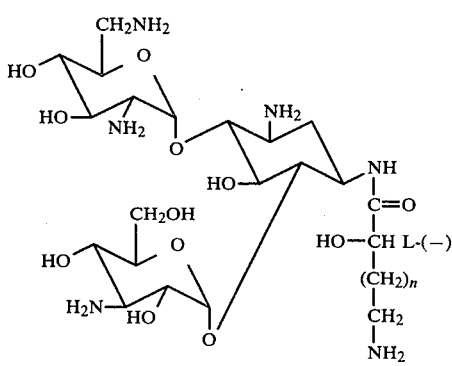

in which n is an integer of from 0 to 2, or a nontoxic pharmaceutically acceptable acid addition salt thereof, which comprises acylating polysilylated kanamycin B with an acylating derivative of the acid of the formula

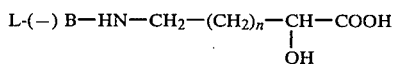

in which n is an integer of from 0 to 2 and B is a conventional amino-blocking group, in a substantially anhydrous organic solvent, and subsequently removing all blocking groups by conventional means; wherein the silyl moieties on the polysilylated kanamycin B are selected from trimethylsilyl, triethylsilyl, tri-n-propylsilyl, methyldichlorosilyl, dimethylchlorosilyl, methyldiethylsilyl, dimethylethylsilyl, dimethyl-t-butylsilyl, phenyldimethylsilyl, benzylmethylethylsilyl, phenylmethylethylsilyl, triphenylsilyl, tri-o-tolylsilyl, tri-p-tolylsilyl and tri-p-dimethylaminophenylsilyl, and the amino blocking group on the acylating derivative of the acid is selected from those of the formulae

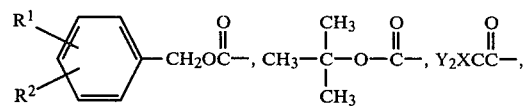

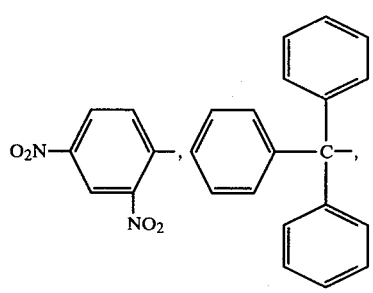

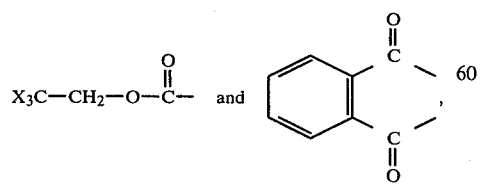

wherein $R^1$ and $R^2$ are alike or different and each is H, F, Cl, Br, $NO_2$, OH, (lower)alkyl or (lower)alkoxy, X is Cl, Br, F or I and Y is H, Cl, Br, F or I.

12. The process of claim 11 wherein the polysilylated kanamycin B contains a conventional non-silyl amino-blocking group selected from those of the formulae

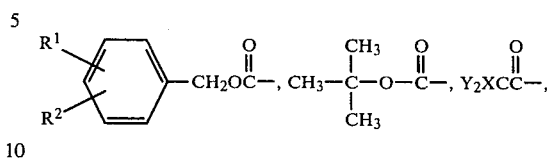

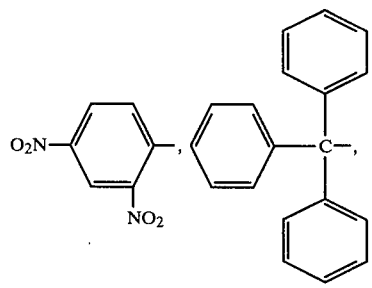

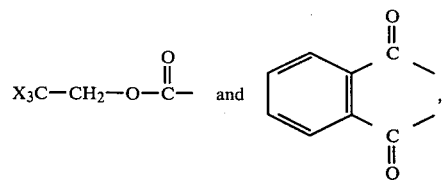

wherein $R^1$ and $R^2$ are alike or different and each is H, F, Cl, Br, $NO_2$, OH, (lower)alkyl or (lower)alkoxy, X is Cl, Br, F or I and Y is H, Cl, Br, F or I on the 6'-amino group.

13. The process of claim 11 wherein the polysilylated kanamycin B contains conventional non-silyl amino-blocking groups selected from those of the formulae

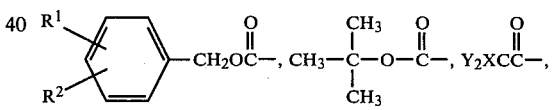

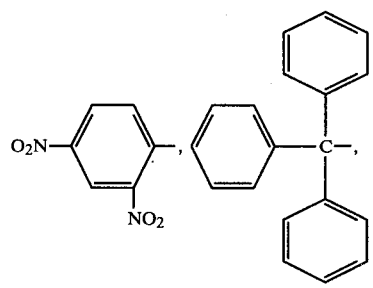

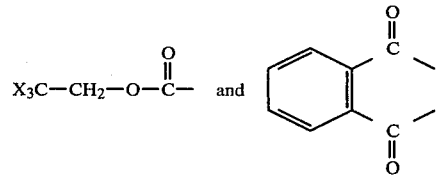

wherein $R^1$ and $R^2$ are alike or different and each is H, F, Cl, Br, $NO_2$, OH, (lower)alkyl or (lower)alkoxy, X is Cl, Br, F or I and Y is H, Cl, Br, F or I on the 3-amino and 6'-amino groups.

14. Polysilylated kanamycin A or B or polysilylated kanamycin A or B containing a conventional non-silyl amino-blocking group on the 3-amino, 6'-amino or 3-amino and 6'-amino groups; wherein the silyl moieties on the polysilylated kanamycin A or B are selected from trimethylsilyl, triethylsilyl, tri-n-propylsilyl, methyldichlorosilyl, dimethylchlorosilyl, methyldiethylsilyl, dimethylethylsilyl, dimethyl-t-butylsilyl, phenyldimethylsilyl, benzylmethylethylsilyl, phenylmethylethylsilyl, triphenylsilyl, tri-o-tolylsilyl, tri-p-tolylsilyl and tri-p-dimethylaminophenylsilyl, and the amino-blocking groups are selected from those of the formulae

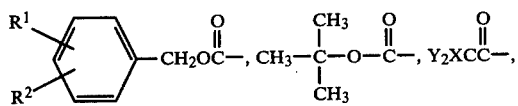

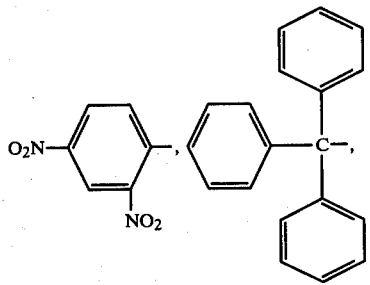

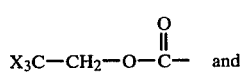 and 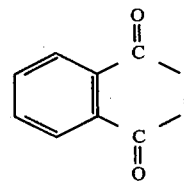

wherein $R^1$ and $R^2$ are alike or different and each is H, F, Cl, Br, $NO_2$, OH, (lower)alkyl or (lower)alkoxy, X is Cl, Br, F or I and Y is H, Cl, Br, F or I.

15. A polysilylated kanamycin A of claim 14 containing an average number of silyl groups per molecule of from 3 to 7.

16. A polysilylated kanamycin A of claim 15 in which the non-silyl amino-blocking group is the carbobenzyloxy group and the silyl groups are trimethylsilyl.

17. A polysilylated kanamycin A of claim 14 containing an average number of silyl groups per molecule of from 3 to 6.

18. A polysilylated kanamycin A of claim 17 in which the non-silyl amino-blocking groups are carbobenzyloxy groups and the silyl groups are trimethylsilyl.

19. Polysilylated kanamycin B having a conventional non-silyl amino-blocking group, as defined in claim 14, on the 6'-amino group and containing an average number of silyl groups, as defined in claim 14, per molecule of from 3 to 7.

20. Polysilylated kanamycin B having conventional non-silyl amino-blocking groups, as defined in claim 14, on the 3-amino and 6'-amino groups, and containing an average number of silyl groups, as defined in claim 14, per molecule of from 3 to 6.

21. A polysilylated kanamycin B of claim 9 or 20 in which the non-silyl amino-blocking group is the carbobenzyloxy group and the silyl groups are trimethylsilyl.

* * * * *

UNITED STATES PATENT AND TRADEMARK OFFICE
CERTIFICATE OF CORRECTION

PATENT NO. : 4,424,343

DATED : January 3, 1984

INVENTOR(S) : Martin J. Cron, et al.

It is certified that error appears in the above—identified patent and that said Letters Patent is hereby corrected as shown below:

In Claim 21, line 1 thereof, the phrase "claim 9 or 20" should read --- claim 19 or 20 ---.

Signed and Sealed this

Twentieth Day of March 1984

[SEAL]

Attest:

Attesting Officer

GERALD J. MOSSINGHOFF

Commissioner of Patents and Trademarks